United States Patent
Klechevsky et al.

(10) Patent No.: US 11,884,934 B2
(45) Date of Patent: Jan. 30, 2024

(54) METHODS AND COMPOSITIONS FOR T CELL ACTIVATION

(71) Applicant: Washington University, St. Louis, MO (US)

(72) Inventors: Eynav Klechevsky, St. Louis, MO (US); Amit Pathak, St. Louis, MO (US); Bapi Sarker, St. Louis, MO (US)

(73) Assignee: Washington University, St. Louis, MO (US)

( * ) Notice: Subject to any disclaimer, the term of this patent is extended or adjusted under 35 U.S.C. 154(b) by 835 days.

(21) Appl. No.: 16/632,717

(22) PCT Filed: Jul. 20, 2018

(86) PCT No.: PCT/US2018/043023
§ 371 (c)(1),
(2) Date: Jan. 21, 2020

(87) PCT Pub. No.: WO2019/018727
PCT Pub. Date: Jan. 24, 2019

(65) Prior Publication Data
US 2021/0163894 A1 Jun. 3, 2021

Related U.S. Application Data

(60) Provisional application No. 62/535,665, filed on Jul. 21, 2017.

(51) Int. Cl.
| | |
|---|---|
| *C12N 5/0784* | (2010.01) |
| *A61P 35/00* | (2006.01) |
| *A61K 9/50* | (2006.01) |
| *A61K 35/17* | (2015.01) |
| *C12N 5/00* | (2006.01) |
| *C12N 5/0783* | (2010.01) |
| *A61K 47/00* | (2006.01) |
| *A61K 47/69* | (2017.01) |
| *C07K 16/28* | (2006.01) |
| *C07K 14/54* | (2006.01) |
| *C07K 14/74* | (2006.01) |
| *C07K 14/715* | (2006.01) |

(52) U.S. Cl.
CPC .......... *C12N 5/0639* (2013.01); *A61K 9/5057* (2013.01); *A61K 9/5068* (2013.01); *A61K 9/5089* (2013.01); *A61K 35/17* (2013.01); *A61K 47/00* (2013.01); *A61K 47/6903* (2017.08); *A61P 35/00* (2018.01); *C07K 14/5443* (2013.01); *C07K 14/70539* (2013.01); *C07K 14/7155* (2013.01); *C07K 16/2818* (2013.01); *C12N 5/0012* (2013.01); *C12N 5/0638* (2013.01); *C12N 2501/2315* (2013.01); *C12N 2501/51* (2013.01); *C12N 2501/998* (2013.01); *C12N 2531/00* (2013.01); *C12N 2533/54* (2013.01); *C12N 2533/74* (2013.01); *C12N 2537/10* (2013.01)

(58) Field of Classification Search
CPC .................................................... C12N 5/0639
See application file for complete search history.

(56) References Cited

U.S. PATENT DOCUMENTS

| | | | |
|---|---|---|---|
| 2013/0202548 A1 | 8/2013 | Rowan et al. | |
| 2015/0056144 A1* | 2/2015 | Aboody | A61K 49/085 |
| | | | 424/9.32 |
| 2015/0366956 A1 | 12/2015 | Mooney et al. | |
| 2016/0008399 A1 | 1/2016 | Stephan | |
| 2017/0081636 A1 | 3/2017 | Kevlahan et al. | |
| 2020/0085971 A1* | 3/2020 | Kevlahan | A61K 47/183 |

FOREIGN PATENT DOCUMENTS

| | | | | |
|---|---|---|---|---|
| WO | WO-2005065121 A2 * | 7/2005 | ............. | A61K 31/28 |
| WO | WO-2016210129 A1 * | 12/2016 | ............. | A61K 35/17 |

OTHER PUBLICATIONS

Ivanovska et al. (Tissue Engineering: Part C 2016 22(7): 708-715) (Year: 2016).*
Anderson Ana C, Joller N, & Kuchroo Vijay K (2016) Lag-3, Tim-3, and TIGIT: Co-inhibitory Receptors with Specialized Functions in Immune Regulation. Immunity 44(5):989-1004.
Bakker AH & Schumacher TNM (2005) MHC multimer technology: current status and future prospects. Current Opinion in Immunology 17(4):428-433.
Banchereau J, Thompson-Snipes L, Zurawski S, Blanck JP, Cao Y, Clayton S, Gorvel JP, Zurawski G, & Klechevsky E (2012) The differential production of cytokines by human Langerhans cells and dermal CD14(+) DCs controls CTL priming. Blood 119(24):5742-5749.
Banchereau J, Zurawski S, Thompson-Snipes L, Blanck J-P, Clayton S, Munk A, Cao Y, Wang Z, Khandelwal S, Hu J, McCoy WH, Palucka KA, Reiter Y, Fremont DH, Zurawski G, Colonna M, Shaw AS, & Klechevsky E (2012) Immunoglobulin-like transcript receptors on human dermal CD14+ dendritic cells act as a CD8-antagonist to control cytotoxic T cell priming. Proceedings of the National Academy of Sciences 109(46):18885-18890.
Boontheekul T, Kong H-J, & Mooney DJ (2005) Controlling alginate gel degradation utilizing partial oxidation and bimodal molecular weight distribution. Biomaterials 26:2455-2465.
Chen DS & Mellman I (2013) Oncology meets immunology: the cancer-immunity cycle. Immunity 39(1):1-10.

(Continued)

Primary Examiner — Peter J Reddig

(57) ABSTRACT

Among the various aspects of the present disclosure is the provision of methods, synthetic DC, and compositions for T cell activation. The present disclosure provides for synthetic dendritic cells (DCs), methods of generating synthetic dendritic cells (DCs), methods of generating T cell-encapsulated gelatin microspheres and microcapsules, methods of activating T cells using synthetic DCs, methods for expanding T cells against individualized antigen-specific mutational antigens using synthetic DCs, and methods of treating a chronic disease (e.g., HIV, HPV) or cancer using the synthetic DCs.

13 Claims, 11 Drawing Sheets

Specification includes a Sequence Listing.

(56) References Cited

OTHER PUBLICATIONS

Cheuk S, Schlums H, Gallais Sérézal I, Martini E, Chiang SC, Marquardt N, Gibbs A, Detlofsson E, Introini A, Forkel M, Höög C, Tjernlund A, Michaëlsson J, Folkersen L, Mjösberg J, Blomqvist L, Ehrström M, Ståhle M, Bryceson YT, & Eidsmo L (2017) CD49a Expression Defines Tissue-Resident CD8+ T Cells Poised for Cytotoxic Function in Human Skin. Immunity 46(2):287-300.

Chu CC, Ali N, Karagiannis P, Di Meglio P, Skowera A, Napolitano L, Barinaga G, Grys K, Sharif-Paghaleh E, Karagiannis SN, Peakman M, Lombardi G, & Nestle FO (2012) Resident CD141 (BDCA3)+ dendritic cells in human skin produce IL-10 and induce regulatory T cells that suppress skin inflammation. J Exp Med 209(5):935-945.

Couzin-Frankel J (2013) Breakthrough of the year 2013. Cancer immunotherapy. Science 342(6165):1432-1433.

De Jong A, Pena-Cruz V, Cheng TY, Clark RA, Van Rhijn I, & Moody DB (2010) CD1a-autoreactive T cells are a normal component of the human alphabeta T cell repertoire. Nat Immunol 11(12):1102-1109.

Denkberg G, Cohen CJ, Segal D, Kirkin AF, & Reiter Y (2000) Recombinant human single-chain MHC-peptide complexes made from E. coli By in vitro refolding: functional single-chain MHC-peptide complexes and tetramers with tumor associated antigens. Eur J Immunol 30(12):3522-3532.

Detsch R, Sarker B, Zehnder T, Frank G, & Boccaccini AR (2015) Advanced alginate-based hydrogels. Materials Today 18:590-591.

Diamond MS, Kinder M, Matsushita H, Mashayekhi M, Dunn GP, Archambault JM, Lee H, Arthur CD, White JM, Kalinke U, Murphy KM, & Schreiber RD (2011) Type I interferon is selectively required by dendritic cells for immune rejection of tumors. J Exp Med 208(10):1989-2003.

Dong H, Strome SE, Salomao DR, Tamura H, & Hirano F (2002) Tumor-associated B7-H1 promotes T-cell apoptosis: a potential mechanism of immune evasion. Nat. Med. 8:793.

Fujita H, Nograles KE, Kikuchi T, Gonzalez J, Carucci JA, & Krueger JG (2009) Human Langerhans cells induce distinct IL-22-producing CD4+ T cells lacking IL-17 production. Proc Natl Acad Sci U S A 106(51):21795-21800.

Gasperini L, Mano JF, & Reis RL (2014) Natural polymers for the microencapsulation of cells. Journal of the Royal Society, Interface / the Royal Society 11:20140817.

Grakoui A, Bromley SK, Sumen C, Davis MM, Shaw AS, Allen PM, & Dustin ML (1999) The immunological synapse: a molecular machine controlling T cell activation. Science 285(5425):221-227.

Gubin MM, Zhang X, Schuster H, Caron E, Ward JP, Noguchi T, Ivanova Y, Hundal J, Arthur CD, Krebber W-J, Mulder GE, Toebes M, Vesely MD, Lam SSK, Korman AJ, Allison JP, Freeman GJ, Sharpe AH, Pearce EL, Schumacher TN, Aebersold R, Rammensee H-G, Melief CJM, Mardis ER, Gillanders WE, Artyomov MN, & Schreiber RD (2014) Checkpoint blockade cancer immunotherapy targets tumour-specific mutant antigens. Nature 515(7528):577-581.

Hildner K, Edelson BT, Purtha WE, Diamond M, Matsushita H, Kohyama M, Calderon B, Schraml BU, Unanue ER, Diamond MS, Schreiber RD, Murphy TL, & Murphy KM (2008) Batf3 deficiency reveals a critical role for CD8alpha+ dendritic cells in cytotoxic T cell immunity. Science 322(5904):1097-1100.

International Search Report and Written Opinion dated Nov. 20, 2018 in corresponding International Application No. PCT/US18/43023 filed Jul. 20, 2018, 15 pages.

Judokusumo E, Tabdanov E, Kumari S, Dustin ML, & Kam LC (2012) Mechanosensing in T lymphocyte activation. Biophys J 102(2):L5-7.

June C, Rosenberg SA, Sadelain M, & Weber JS (2012) T-cell therapy at the threshold. Nat Biotechnol 30(7):611-614.

Klebanoff CA, Khong HT, Antony PA, Palmer DC, & Restifo NP (2005) Sinks, suppressors and antigen presenters: how lymphodepletion enhances T cell-mediated tumor immunotherapy. Trends Immunol 26(2):111-117.

Klechevsky E (2013) Human dendritic cells—stars in the skin. European Journal of Immunology 43(12):3147-3155.

Klechevsky E, Gallegos M, Denkberg G, Palucka K, Banchereau J, Cohen C, & Reiter Y (2008) Antitumor Activity of Immunotoxins with T-Cell Receptor-like Specificity against Human Melanoma Xenografts. Cancer Research 68(15):6360.

Klechevsky E, Morita R, Liu M, Cao Y, Coquery S, Thompson-Snipes L, Briere F, Chaussabel D, Zurawski G, Palucka AK, Reiter Y, Banchereau J, & Ueno H (2008) Functional specializations of human epidermal Langerhans cells and CD14+ dermal dendritic cells. Immunity 29(3):497-510.

Kong H, Smith MK, & Mooney DJ (2003) Designing alginate hydrogels to maintain viability of immobilized cells. Biomaterials 24:4023-4029.

Kroemer G & Galluzzi L (2015) Combinatorial immunotherapy with checkpoint blockers solves the problem of metastatic melanoma— An exclamation sign with a question mark. Oncoimmunology, 4(7):e1058037.

Leach DR, Krummel MF, & Allison JP (1996) Enhancement of antitumor immunity by CTLA-4 blockade. Science 271(5256):1734-1736.

Lenz A, Heine M, Schuler G, & Romani N (1993) Human and murine dermis contain dendritic cells. Isolation by means of a novel method and phenotypical and functional characterization. J Clin Invest 92(6):2587-2596.

Mackay JL & Kumar S (2013) Measuring the elastic properties of living cells with atomic force microscopy indentation. Methods Mol Biol 931:313-329.

Mellman I, Coukos G, & Dranoff G (2011) Cancer immunotherapy comes of age. Nature 480(7378):480-489.

Monach PA, Meredith SC, Siegel CT, & Schreiber H (1995) A unique tumor antigen produced by a single amino acid substitution. Immunity 2(1):45-59.

Nasrollahi S & Pathak A (2016) Topographic confinement of epithelial clusters induces epithelial-to-mesenchymal transition in compliant matrices. Sci Rep 6:18831.

Nestle FO, Zheng XG, Thompson CB, Turka LA, & Nickoloff BJ (1993) Characterization of dermal dendritic cells obtained from normal human skin reveals phenotypic and functionally distinctive subsets. J Immunol 151(11):6535-6545.

O'Connor RS, Hao X, Shen K, Bashour K, Akimova T, Hancock WW, Kam LC, & Milone MC (2012) Substrate rigidity regulates human T cell activation and proliferation. J Immunol 189(3):1330-1339.

Pathak A & Kumar S (2011) From Molecular Signal Activation to Locomotion: An Integrated, Multiscale Analysis of Cell Motility on Defined Matrices. PLoS One 6(3):e18423.

Pathak A & Kumar S (2012) Independent regulation of tumor cell migration by matrix stiffness and confinement. Proceedings of the National Academy of Sciences 109(26):10334-10339.

Pathak A & Kumar S (2013) Transforming potential and matrix stiffness co-regulate confinement sensitivity of tumor cell migration. Integrative Biology 5(8):1067-1075.

Penel-Sotirakis K, Simonazzi E, Peguet-Navarro J, & Rozieres A (2012) Differential capacity of human skin dendritic cells to polarize CD4+ T cells into IL-17, IL-21 and IL-22 producing cells. PLoS One 7(11):e45680.

Purtic B, Pitcher LA, van Oers NS, & Wulfing C (2005) T cell receptor (TCR) clustering in the immunological synapse integrates TCR and costimulatory signaling in selected T cells. Proc Natl Acad Sci U S A 102(8):2904-2909.

Reis e Sousa C (2006) Dendritic cells in a mature age. Nat Rev Immunol 6(6):476-483.

Rodenko B, Toebes M, Hadrup SR, van Esch WJ, Molenaar AM, Schumacher TN, & Ovaa H (2006) Generation of peptide-MHC class I complexes through UV-mediated ligand exchange. Nat Protoc 1(3):1120-1132.

Rowley JA, Madlambayan G, & Mooney DJ (1999) Alginate hydrogels as synthetic extracellular matrix materials. Biomaterials 20:45-53.

(56) References Cited

OTHER PUBLICATIONS

Sakai S, Ito S, & Kawakami K (2010) Calcium alginate microcapsules with spherical liquid cores templated by gelatin microparticles for mass production of multicellular spheroids. Acta Biomater 6(8):3132-3137.

Sarker B, Papageorgiou DG, Silva R, Zehnder T, Gul-E-Noor F, Bertmer M, Kaschta J, Chrissafis K, Detsch R, & Boccaccini AR (2014) Fabrication of alginate-gelatin crosslinked hydrogel microcapsules and evaluation of the microstructure and physico-chemical properties. Journal of Materials Chemistry B 2:1470.

Sarker B, Singh R, Silva R, Roether JA, Kaschta J, Detsch R, Schubert DW, Cicha I, & Boccaccini AR (2014) Evaluation of fibroblasts adhesion and proliferation on alginate-gelatin crosslinked hydrogel. PLoS One 9:e107952.

Sarker B, Rompf J, Silva R, Lang N, Detsch R, Kaschta J, Fabry B, & Boccaccini AR (2015) Alginate-based hydrogels with improved adhesive properties for cell encapsulation. International Journal of Biological Macromolecules 78:72-78.

Sarker et al., Oxidized Alginate-Gelatin Hydrogel: A Favorable Matrix for Growth and Osteogenic Differentiation of Adipose-Derived Stem Cells in 3D, CS Biomater. Sci. Eng. Jun. 15, 2017, 3, 8, 1730-1737. https://doi.org/10.1021/acsbiomaterials.7b00188.

Schreiber RD, Old LJ, & Smyth MJ (2011) Cancer immunoediting: integrating immunity's roles in cancer suppression and promotion. Science 331(6024):1565-1570.

Schumacher TN & Schreiber RD (2015) Neoantigens in cancer immunotherapy. Science 348(6230):69-74.

Seder RA, Darrah PA, & Roederer M (2008) T-cell quality in memory and protection: implications for vaccine design. Nat Rev Immunol 8(4):247-258.

Stephan SB, Taber AM, Jileaeva I, Pegues EP, Sentman CL, & Stephan MT (2015) Biopolymer implants enhance the efficacy of adoptive T-cell therapy. Nat Biotechnol 33(1):97-101.

Woo EY, Chu CS, Goletz TJ, Schlienger K, Yeh H, Coukos G, Rubin SC, Kaiser LR, & June CH (2001) Regulatory CD4(+)CD25(+) T cells in tumors from patients with early-stage non-small cell lung cancer and late-stage ovarian cancer. Cancer Res 61(12):4766-4772.

Yuan J, Gnjatic S, Li H, Powel S, Gallardo HF, Ritter E, Ku GY, Jungbluth AA, Segal NH, Rasalan TS, Manukian G, Xu Y, Roman R-A, Terzulli SL, Heywood M, Pogoriler E, Ritter G, Old LJ, Allison JP, & Wolchok JD (2008) CTLA-4 blockade enhances polyfunctional NY-ESO-1 specific T cell responses in metastatic melanoma patients with clinical benefit. Proceedings of the National Academy of Sciences 105(51):20410-20415.

Zaba LC, Fuentes-Duculan J, Steinman RM, Krueger JG, & Lowes MA (2007) Normal human dermis contains distinct populations of CD11c+BDCA-1+ dendritic cells and CD163+FXIIIA+ macrophages. J Clin Invest 117(9):2517-2525.

\* cited by examiner

Example 2

Bio-mechanically optimized Synthetic DCs

Example 3

Bio-mechanically optimized Synthetic DCs

Klechevsky et al. Immunity 2008

Banchereau et al. Blood 2012

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: synthetic peptide

<400> SEQUENCE: 1

Glu Leu Ala Gly Ile Gly Ile Leu Thr Val
1               5                   10

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Ala Ala Gly Ile Gly Ile Leu Thr Val
1               5
```

METHODS AND COMPOSITIONS FOR T CELL ACTIVATION

CROSS-REFERENCE TO RELATED APPLICATIONS

This application is a National Stage of International Application No. PCT/US18/43023, filed 20 Jul. 2018, which claims priority from U.S. Provisional Application Ser. No. 62/535,665 filed on 21 Jul. 2017, which is incorporated herein by reference in its entirety.

STATEMENT REGARDING FEDERALLY SPONSORED RESEARCH OR DEVELOPMENT

This invention was made with government support under EB024767 awarded by the National Institutes of Health. The government has certain rights in the invention.

MATERIAL INCORPORATED-BY-REFERENCE

The Sequence Listing, which is a part of the present disclosure, includes a computer-readable form comprising nucleotide and/or amino acid sequences of the present invention (file name 017391-WO sequence listing ST25.txt created on 18 Sep. 2017; 630 bytes). The subject matter of the Sequence Listing is incorporated herein by reference in its entirety.

FIELD OF THE INVENTION

The present disclosure generally relates to compositions of synthetic immune cells and the methods of use and production thereof.

BACKGROUND OF THE INVENTION

In the last decade there has been an explosive development in the fields of tumor immunology and immunotherapy. There is now much known about the chemical nature of tumor antigens, the ability of the immune system (cells, molecules) to both prevent and promote cancer development, and the critical role of immunosuppressive networks in blocking antitumor immune responses. Cancer immunotherapy attempts to harness the power and specificity of the immune system to treat tumors. An efficient and robust anticancer immune response critically depends on robust activation and proliferation of helper and cytotoxic T cells and a persistent memory response. Yet, the development of therapeutically effective cancer vaccines remains an unfulfilled promise.

A major obstacle in developing effective cell based therapies is the ability to robustly expand long-lived tumor specific T cells. Because each patient's tumor displays unique mutated epitopes (which are mostly of low affinity), there is clearly a need for expanding these unique antigen-specific T cells for each patient. In addition, cancer patients display a high number and function of $CD4^+$ $CD25^+$ Tregs at the tumor site. The in vivo depletion of Tregs enhances the antitumor effects of adoptively transferred effector T cells. Thus, there is a pressing need to develop a method to expand T cells with an effector rather than a regulatory function.

The current in vivo and ex vivo methods of expansion of T cells obtained from patients rely on non-specific exposure to T cell receptor (TCR) stimuli and a high dose of IL-2. These methods allow the hyperactivation of regulatory T cells (Tregs), which are known to suppress tumor-specific responses. New immunotherapeutic approaches that block immunosuppressive molecules on T cells have been shown to enhance anti-tumor immune responses in approximately 30% of treated cancer patients. Despite this important progress, the development of highly effective cancer immunotherapies remains a challenge. In part, the progress on this front has been hampered by the difficulty in expanding long-lived effector $CD8^+$ T cells that are specific to unique peptides presented by the tumors.

SUMMARY OF THE INVENTION

Among the various aspects of the present disclosure is the provision of methods and compositions for T cell activation. Briefly, the present disclosure is directed to synthetic dendritic cells (DCs), methods of generating synthetic dendritic cells (DCs), methods of generating T cell-encapsulated gelatin microspheres and microcapsules, methods of activating T cells, methods for expanding T cells against individualized tumor-specific mutational antigens, and methods of treating cancer using the synthetic DCs.

An aspect of the present disclosure provides for a synthetic dendritic cell (synthetic DC). In some embodiments, the synthetic DC comprises a delivery agent; a linker; a binding moiety; and/or a T cell activation agent, wherein, the linker is coupled to the delivery agent; the binding moiety is coupled to the linker and the T cell activation agent; or the synthetic DC is capable of initiating the activation and expansion of T cells.

In some embodiments, the T cell activation agent comprises one or more compositions selected from the group consisting of MHC, pMHC, anti-CD28 (αCD28), Interleukin 15 (IL15)/IL-15Rα, IL-2, IL-7, IL-12, CD1a, CD1c, CD1d, CD70, CD40, CD5, CD80, or CD86.

In some embodiments, one or more components of the T cell activation agent is conjugated to a peptide or peptide tetramer.

In some embodiments, the delivery agent comprises an oxidized alginate-gelatin covalently cross-linked (ADA-GEL) hydrogel.

In some embodiments, the linker comprises a bi-functional hydrophilic polyethylene glycol (PEG)-based linker (optionally, a biotin-$PEG_4$-hydrazide).

In some embodiments, the delivery agent comprises a soft, flexible, or non-rigid matrix; the delivery agent comprises a hydrogel, an alginate gelatin gel, or a 3D microcapsule; the delivery agent has a stiffness between about 1 kPa and about 30 kPa; the linker is flexible; the linker provides an extended reach; the linker comprises PEG, optionally, PEG4; the linker provides a flexible, extended reach to provide improved access to a T cell; the T cell activation agent comprises one or more compositions selected from the group consisting of MHC, pMHC, anti-CD28 (αCD28), or Interleukin 15 (IL15)/IL-15Rα, IL-2, IL-7, IL-12, CD1a, CD1c, CD1d, CD70, CD40, CD5, CD80, or CD86, the T cell activation agent is multimeric (e.g., a pentamer); or the binding moiety comprises avidin, streptavidin, or neutravidin.

In some embodiments, the synthetic DC comprises one or more agents capable of neutralizing negative co-stimulatory regulators on T cells selected from the group consisting of anti-CTLA-4, anti-PDL-1, anti-PD-1, anti-IL13R, or anti-IL4R.

Another aspect of the present disclosure provides for a method of generating a synthetic dendritic cell (DC). In some embodiments, the method comprises (i) providing a delivery agent; (ii) providing a linker; (iii) providing a binding moiety; (iv) providing one or more T cell activation agents; (v) coupling the linker to the delivery agent; (vi) coupling the linker to the binding moiety; and/or (vii) coupling the binding moiety to the one or more T cell activation agents.

Another aspect of the present disclosure provides for a method of generating a T cell-encapsulated gelatin microsphere. In some embodiments, the method comprises (i) providing a T cell dispersion in a gelatin solution; (ii) extruding the gelatin solution dispersed with T cells from a needle into a co-flowing immiscible stream of lecithin containing liquid paraffin, forming a drop; (iii) gelling the drop at a temperature for a period of time sufficient for the extruded gel solution to gel, forming a T cell containing gelatin; and/or (iv) removing the paraffin.

In some embodiments, the T cell dispersion in a gelatin solution is at a density of about $1 \times 10^7$ cells/mL; the needle has a diameter of about 27 gauge; the lecithin containing liquid paraffin is at a temperature of about 37° C.; the gelling is performed at a temperature of about 0° C. or in an ice bath for about 10 minutes; the extrusion is performed at a rate sufficient to form a microsphere and the rate can be varied to form different sized microspheres; or the removing of the paraffin comprises washing the microsphere with a 4° C. CF-KRH solution for a period of time sufficient to remove all or substantially all the paraffin.

Another aspect of the present disclosure provides for a method of encapsulating a microsphere or forming a microcapsule. In some embodiments, the method comprises (i) providing a microsphere comprising T cells; (ii) providing a synthetic DC; (iii) providing a delivery agent; (iv) providing a high voltage DC generator comprising a first end and a second end; (iv) combining the microsphere, the synthetic DC, and the delivery agent resulting in a solution; (v) extruding the solution through a needle operably connected to the first end of the high voltage DC generator; (iv) providing a salt bath operably connected to the second end of a high voltage generator; (v) dropping the extruded solution into a gelatin bath; and/or (vi) applying a voltage to the needle and the gelatin bath.

In some embodiments, the microsphere is prepared according to the method described above; the synthetic DC is prepared according to any method described above; the delivery agent comprises a hydrogel, optionally, ADA; the needle has a diameter of about 26 gauge; or the salt bath comprises a $Ca_2Cl$, wherein the $Ca_2Cl$ concentration can be varied to change characteristics of the microcapsule.

In some embodiments, the method comprises extruding the solution and dropping into the gelation bath under an applied voltage resulting in a T cell-containing gelatin microspheres embedded within the delivery agent.

In some embodiments, the method comprises gelling the microcapsules in the salt bath for a period of time, optionally about 10 min, suitable for ionic gelation; or washing the salt bath solution from the microcapsules with a serum-free cell culture medium.

In some embodiments, the method comprises liquification or melting of the microcapsule to enable the T cell to contact the delivery agent (optionally, an ADA matrix) containing the synthetic DCs.

In some embodiments, the method comprises incubating the T cells in the microcapsule for a period of time sufficient for the T cells to activate, expand, or proliferate (optionally, about 3 to 10 days); or dissolving the delivery agent (optionally, hydrogel) using a dissolving agent (optionally, a calcium chelator, sodium citrate, or alginate lyase), wherein the method results in activated T cells.

In some embodiments, the method comprises implantation of the activated T cells at a tumor site.

Another aspect of the present disclosure provides for a method of activating T cells. In some embodiments, the method comprises (i) providing a synthetic DC according to claim 1; and/or (ii) providing a T cell in fluid contact with the synthetic DC.

Another aspect of the present disclosure provides for a method for expanding T cells against individualized tumor-specific mutational antigens or shared antigen. In some embodiments, the method comprises (i) providing T cells, optionally from a tumor biopsy or blood; (ii) providing a synthetic DC described above; (iii) activating the T cells comprising contacting the T cell and the synthetic DC; (iv) incubating the T cells and the synthetic DC for a period of time sufficient to induce T cell activation; and/or (v) administering the activated T cells to a subject.

Another aspect of the present disclosure provides for a method of treating cancer or chronic disease (e.g., chronic viral infection, HCV, HIV) in a subject in need thereof. In some embodiments, the method comprises (i) providing T cells, optionally from a tumor biopsy or blood; (ii) providing a synthetic DC of claim 1; (iii) activating the T cells comprising contacting the T cell and the synthetic DC; (iv) incubating the T cells and the synthetic DCs for a period of time sufficient to induce T cell activation; and/or (ii) administering the activated T cells to the subject.

In some embodiments, the T cell activation agent comprises one or more compositions selected from the group consisting of MHC, pMHC, anti-CD28 ($\alpha$CD28), Interleukin 15 (IL15)/IL-15R$\alpha$, IL-2, IL-7, IL-12, CD1a, CD1c, CD1d, CD70, CD40, CD5, CD80, or CD86.

In some embodiments, the synthetic DCs enable a high-throughput production of subject-specific T cells.

In some embodiments, the delivery agent is mechanically optimized to mimic a DC.

In some embodiments, the method comprises one or more components of the T cell activation agent is conjugated to a peptide or peptide tetramer.

In some embodiments, the delivery agent comprises an oxidized alginate-gelatin covalently cross-linked (ADA-GEL) hydrogel.

In some embodiments, the linker comprises a bi-functional hydrophilic polyethylene glycol (PEG)-based linker (optionally, a biotin-$PEG_4$-hydrazide).

In some embodiments, the delivery agent comprises a soft, flexible, or non-rigid matrix; the delivery agent comprises a hydrogel, an alginate gelatin gel, or a 3D microcapsule; the delivery agent has a stiffness between about 1 kPa and about 30 kPa; the linker is flexible; the linker provides an extended reach; the linker comprises PEG, optionally, PEG4; the linker provides a flexible, extended reach to provide improved access to a T cell; the T cell activation agent comprises one or more compositions selected from the group consisting of MHC, pMHC, anti-CD28 ($\alpha$CD28), or Interleukin 15 (IL15)/IL-15R$\alpha$, IL-2, IL-7, IL-12, CD1a, CD1c, CD1d, CD70, CD40, CD5, CD80, or CD86; the T cell activation agent is multimeric; or the binding moiety comprises avidin, streptavidin, or neutravidin.

In some embodiments, the method of synthetic DC comprises one or more agents capable of neutralizing negative co-stimulatory regulators on T cells selected from the group consisting of anti-CTLA-4, anti-PDL-1, anti-PD-1, anti-IL13R, or anti-IL4R.

In some embodiments, the T cells are provided by a subject in need of a therapeutic treatment.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A shows the natural T cell-DC interaction through TCR, CD28 and IL-15R. FIG. 1B depicts T cell activation on 2D alginate-gelatin substrates of tunable stiffness and DC-like properties. FIG. 1C is a schematic showing the expansion and collection of T cells in 3D microcapsules.

FIG. 5A is a schematic showing the fabrication of T cell-embedded gelatin microspheres with a co-axial droplet generator. FIG. 5B is a schematic depicting the encapsulation, proliferation and activation of T cells in hollow-core hydrogel microcapsules via interaction with biotinylated pMHC, biotinylated αCD28 antibodies, and IL-15/1L-15Rα in a 3D environment.

DETAILED DESCRIPTION OF THE INVENTION

Figure 1A:
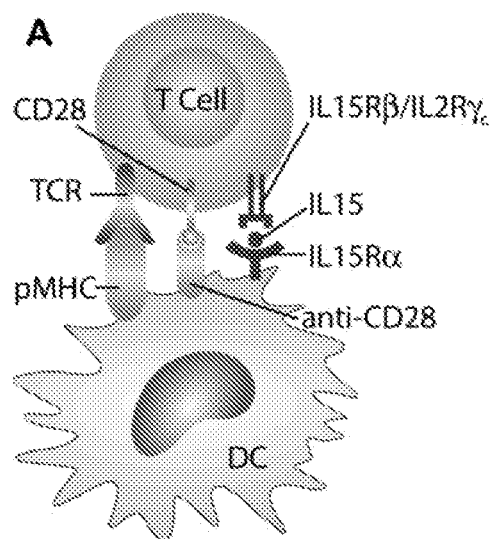
FIG. 1A-FIG. 1C is a series of schematics depicting the interaction of T cells with natural or synthetic dendritic cells (DCs).

The present disclosure is based, at least in part, on the discovery that mechanically optimized synthetic dendritic cells can be used for the expansion of antigen-specific T cells. As described herein, a new paradigm for expanding T cells against individualized tumor-specific mutational antigens through interaction with novel mechanically optimized synthetic DCs has been discovered. Furthermore, as shown herein, combining signals allows the most efficient expansion of low affinity peptides, which represent a model for neo epitopes generated from cancer cell-mutated proteins. As such, the present disclosure provides for a new method for expanding T cells against individualized tumor-specific mutational antigens and provides for enhanced clustering of DC mimicking molecules due to soft matrices, extended reach of linker, and a multimeric T cell activation agent (e.g., pMHC) for binding.

The current in vivo and ex vivo methods of expansion of T cells obtained from patients rely on non-specific exposure to T cell receptor (TCR) stimuli and a high dose of IL-2. The challenge is in the difficult expansion of long-lived effector CD8$^+$ T cells that are specific to unique peptides presented by the tumors.

In contrast with existing T cell expansion platforms (rigid platforms), the presently disclosed "synthetic DC" can be tailored for individual patients by expanding their unique neo-epitopes (over varying matrix stiffness).

Novel integration of three factors for enhanced clustering of DC-mimicking molecules are described herein, for example, (1) flexibility of soft matrices, (2) extended reach due to a linker, (3) multimeric pMHC for increased probability of binding.

The presently described compositions and methods can facilitate the development of a novel personalized human cancer immunotherapy approach that will be modular, be cost effective, and have high therapeutic efficacy.

Cancer Immunotherapy

Immunotherapy is a rapidly emerging field and it fundamentally relies on large quantities of immune cells. The current in vivo and ex vivo methods of expansion of T cells obtained from patients rely on non-specific exposure to T cell receptors (TCR) stimuli. These methods allow the hyperactivation of regulatory T cells (Tregs), which are known to suppress tumor-specific responses. The presently disclosed compositions and methods enable high-throughput production of activated T cells specific to sub-dominant tumor-associated antigens. In contrast with existing T cell expansion platforms, the proposed "synthetic DC" can be tailored for individual patients by expanding their unique neo-epitopes. Furthermore, the existing platforms of DC-mimicking properties are made of rigid materials, which disable the movement of effector molecules required for TCR clustering and thus remain inefficient in activating T cells. Overall these synthetic DCs made of "mechanically-optimized" soft matrices can maximize the expansion of antigen-specific effector T cells.

Cancer immunotherapy attempts to harness the power and specificity of the immune system to treat tumors. An efficient and robust anti-cancer immune response critically depends on robust activation and proliferation of helper and cytotoxic T cells and a persistent memory response. The current in vivo and ex vivo methods of expansion of T cells obtained from patients rely on non-specific exposure to T cell receptor (TCR) stimuli and a high dose of IL-2. These methods allow the hyperactivation of regulatory T cells (Tregs), which are known to suppress tumor-specific responses. New immunotherapeutic approaches that block immunosuppressive molecules on T cells have been shown to enhance anti-tumor immune responses in approximately 30% of treated cancer patients. Despite this important progress, the development of highly effective cancer immunotherapies remains a challenge. In part, the progress on this front has been hampered by the difficulty in expanding long-lived effector CD8$^+$ T cells that are specific to unique peptides presented by the tumors.

Synthetic Dendritic Cells

The present disclosure provides for mechanically-optimized synthetic dendritic cells for the expansion of antigen-specific T cells.

Provided herein are compositions and methods that enable high-throughput production of patient specific T cells.

The present disclosure further provides for a use of a mechanically optimized matrix (e.g., alginate-gelatin (soft)) to mimic dendritic cells (synthetic DCs) for the expansion of antigen-specific effector T cells. Combined with the matrix can be a linker (e.g., PEG) and a binding moiety (e.g., Streptavidin) conjugated to a T cell activation agent (e.g., a multimeric pMHC, an anti-CD28 monoclonal antibody, IL-15, CD70, CD40, CD5, 4-1BBL, or OX40L) for the activation and expansion of T cells.

Dendritic Cells

Dendritic cells (DC) are responsible for initiating most antigen-specific immune responses. DCs form an immunological synapse with T cells which is orchestrated by three main signals and forms the basis for antigen-specific immune responses (see e.g., FIG. 1A). First, DCs present peptide bound major histocompatibility complex (pMHC) recognized by the T cell receptor (TCR). Co-stimulatory molecules B7-1 and B7-2 on the DCs provide the second signal for T cell activation, which enhance memory and prevent immune tolerance. Finally, the DCs produce soluble cytokines (IL-15). However, T cell activation can be profoundly skewed by inhibitory molecule-ligation (CTLA-4, PDL-1, PD-1, IL13R, or IL4R) as often happens in cancer.

DCs are heterogeneous and contain distinct subsets with different phenotype and functions. Investigations of human DCs in skin, a site for most vaccine delivery, have shown that the cytokines produced by these DCs as well as their surface receptors control the direction of their response. Specifically, Example 1 shows that IL-15 produced by Langerhans cells (LCs) (DCs that populate the upper layer of the skin) is critical for their ability to prime CTL responses, including activating high avidity CTLs and killing tumor cells, even those with low amounts of antigen—a desired immune response in cancer. DC cytokines such as IL-10 or inhibitory receptors such as the ILT receptor family that are expressed on dermal DCs can actively inhibit immunity. A viable synthetic DC should incorporate all the features of T cell-activating DCs without the regulatory components.

As described herein, the present disclosure provides for the examination of the capacity of human skin DC subsets to activate cytotoxic T lymphocyte (CTL) responses; it was discovered that epidermal DCs were the most efficient at activating high avidity CTLs and killing tumor cells, even those with low amounts of antigen. In order to enable high-throughput production of CTLs specific to sub-dominant tumor-associated antigens, the development of matrices that emulate these epidermal DCs are provided in Examples 2 and 3. In contrast with the existing T cell expansion platforms, the 'synthetic DCs' as described herein can be tailored for individual patients by expanding their unique neo-epitopes. Furthermore, the existing platforms of DC-mimicking properties are made of rigid materials, which disable the movement of effector molecules required for TCR clustering and thus remain inefficient in activating T cells. Separately, it has been shown that T cells proliferate in a mechanosensitive manner. Provided here are synthetic DCs made of 'mechanically-optimized' soft matrices can maximize the expansion of antigen-specific effector T cells.

Figure 1B:
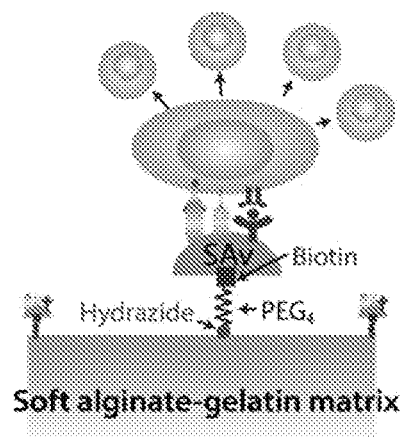
Figure 10:
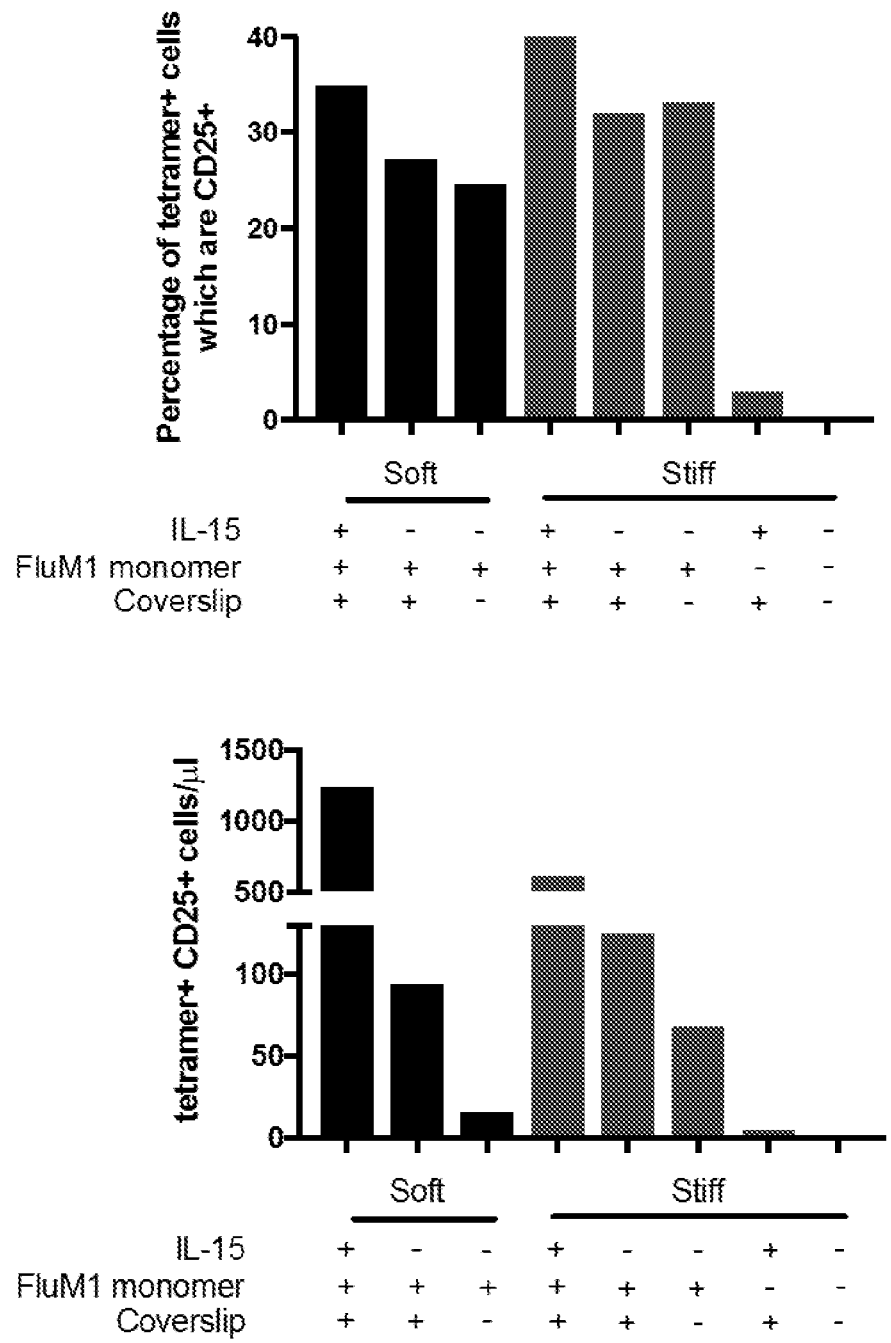
FIG. 10 shows a bar graph illustrating the percentage of tetramer+ cells which are CD25+ (top) and a bar graph illustrating the concentration of tetramer+CD25+ cells (bottom).

There is a substantial need for mechanically optimized synthetic DCs. Recent studies have shown that softer substrates stimulate greater proliferation of human CD4$^+$ and CD8$^+$ T cells. Combining softer matrices with long-chain linkers and multimeric pMHC could enhance the flexibility of effector molecules required for TCR clustering and thus promote T cell activation. Thus, there is a need to move beyond the standard hard materials, such as polystyrene plastic, for culturing T cells and develop softer culture scaffolds optimized for maximal T cell expansion. Example 2 utilizes 2D substrates that allow precise control over matrix stiffness and easy validation of T cell expansion (see e.g., FIG. 1B). While 2D substrates work well for straightforward expansion of T cells, the delivery of T cells near the tumor site may be more accessible through T cells encapsulated within implantable 3D microcapsules, as described in Example 3 (see e.g. FIG. 10). Both 2D and 3D forms of synthetic DC platforms—can cover a wide variety of potential applications.

Figure 1C:
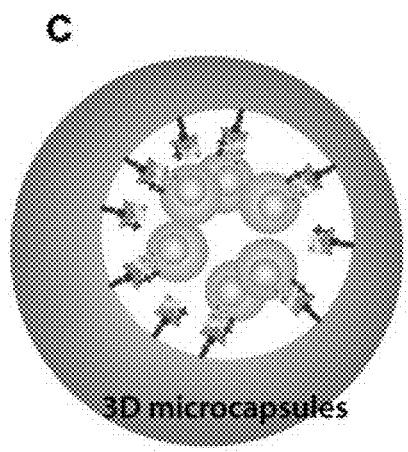

Example 2 provides for the development of mechanically optimized synthetic DCs providing three signals for efficient T cell expansion. An alginate-gelatin based 2D substrate is fabricated and a biotin-PEG$_4$ hydrazide linker was included to enhance the flexibility of attached molecules. Through Streptavidin (SAv), a multimeric pMHC is conjugated, bearing a high or low affinity peptide (signal 1). Also attached to SAv is an anti-CD28 monoclonal antibody (signal 2) and interleukin 15 (IL15)/IL-15Rα complex, along with soluble checkpoint blockade inhibitors such as anti-CTLA-4 and anti-PD-1 (signal 3) (see e.g., FIG. 1). Specific T cell expansion is measured using peptide MHC-tetramers after 7-10 days. The capacity of these cells to recognize and kill tumor cells is assessed, as well as the expression of memory and effector molecules. The matrix stiffness can be varied between 1-30 kPa to maximize clustering of pMHC, anti-CD28 antibody and cytokine-receptor complex for maximal contact with the T cells. T cell expansion is compared across varying matrix stiffness.

Example 3 provides for the fabrication of stiffness-optimized synthetic micro-DCs for T cell growth in the form of 3D microcapsules. To enhance portability of the expanded T cells, alginate-gelatin based 3D micro-DCs are fabricated as micro-capsules of a matrix stiffness optimized in Example 2. The three signals (as in Example 2) are conjugated into the 3D matrix environment, which then is used to encapsulate T cells. An adoptive T cell transfer into nude mice bearing human tumors is used to evaluate the capacity of the expanded antigen-specific T cells to kill an established tumor in-vivo bearing a low affinity antigen, which is also expressed at low abundance.

Delivery Agent

The delivery agent can be a substrate comprising a matrix for activation, expansion, and delivery of T cells for tumor treatment.

The matrix can comprise a hydrogel. For example, the hydrogel can be any naturally-derived hydrogel found to be appropriate for cell encapsulation due to their excellent biocompatibility, biodegradability, and very low cytotoxicity. For example, the hydrogel can be an alginate, an alginate di-aldehyde (ADA), Gelatin (GEL), or an ADA-GEL. As another example, the delivery agent can comprise an oxidized alginate-gelatin covalently cross-linked (ADA-GEL) hydrogel. As another example, the hydrogel can be a polyacrylamide (PA) hydrogel.

Figure 5A:
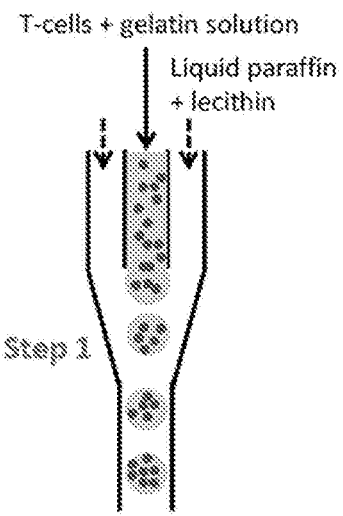
FIG. 5A-FIG. 5B is a series of schematics depicting T cell activation through use of gelatin microspheres.
Figure 5B:
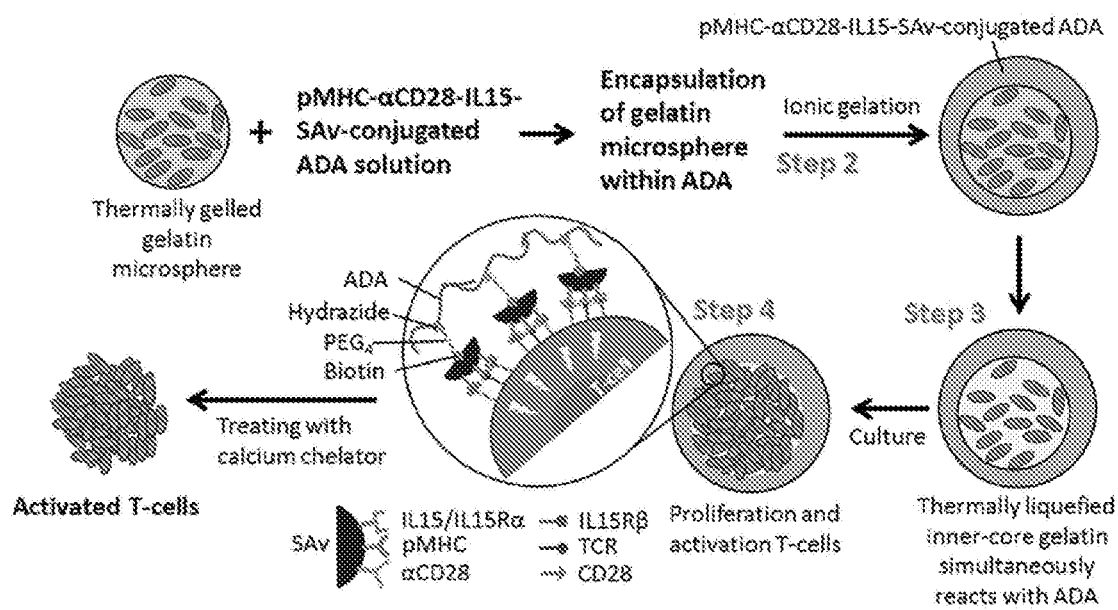

As another example, the matrix can also be formed into a 3D microcapsule (see e.g., FIG. 5A and FIG. 5B).

The matrix stiffness can be designed to vary between 1-30 kPa to modulate (e.g., maximize) clustering. The matrix can be flexible, soft, or non-rigid. For example, the gel stiffness can be tuned through the calcium concentration of a hardening solution. As another example, the stiffness can also be tuned by modulating a ratio of matrix components (e.g., the ratio of ADA and GEL). As another example, the stiffness of a hydrogel (e.g., an ADA-GEL hydrogel) can also be varied by tuning the degree of oxidation (e.g., oxidation of ADA).

3D Microcapsules

The delivery agent can be a 3D microcapsule. Example 3 provides for the formation of 3D microcapsules. First, a thermally gelled microsphere can be generated containing T cells.

The T cell-containing microsphere can be added to a delivery agent (e.g., hydrogel) containing synthetic DCs to form a T cell containing microsphere encapsulated in a synthetic DC containing delivery agent (e.g., hydrogel) (see e.g., FIG. 5B). The microsphere can be produced by ionically gelating a delivery agent (e.g., hydrogel) to the surface of the microsphere. The thermally gelled microsphere containing the T cells can then be melted (e.g., at 37° C.) to allow for the contact of the synthetic DCs and the T cells resulting in T cell activation.

The T cells are allowed to incubate in the 3D microcapsule for a period of time sufficient to activate, expand, or proliferate the T cells (e.g., 3 to 5 days).

The delivery agent/microsphere shell (e.g., hydrogel) can then be dissolved using a dissolving agent (e.g., a calcium chelator (e.g. sodium citrate) or alginate lyase).

The T cells can be isolated from a biological sample of a subject. For example, the biological sample can be blood or skin or a tumor biopsy.

Linker

As described herein, a linker can be used to attach a binding moiety (e.g., biotin binding protein conjugate) to a delivery agent (e.g., a hydrogel). A linker can be any composition used to conjugate a delivery agent to a binding agent (e.g., conjugate a streptavidin to a hydrogel).

A linker group can be any linker group suitable for use to conjugate a delivery agent to a binding agent. For example, the linker can conjugate an alginate-gelatin hydrogel to streptavidin. For example, the streptavidin can interact with the linker through biotinylation of the linker. As another example, the linker can comprise a poly(ethylene glycol) (PEG) derivative. In one embodiment, the linker can be a flexible linker that comprises one or more PEG monomers, e.g., four PEG monomers ($PEG_4$). In other embodiments, the flexible linker can consist of two to ten PEG monomers. As another example, the linker can comprise PEG, TA-PEG-Maleimide, TA-PEG-OMe, or TA-PEG. As another example, a linker can comprise an isothiocyanate group, a carboxylic acid or carboxylate group, a dendrimer, a dendron, Fmoc-protected-2,3-diaminopropanoic acid, ascorbic acid, a silane linker, minopropyltrimethoxysilane (APTMS), or dopamine.

In one embodiment the linker can be covalently coupled to the hydrogel using a hydrazide group, which forms a hydrazone bond between the linker and the aldehyde of the ADA gel. Other covalent coupling methods can use or employ the use of 2 thiol groups, 2 primary amines, a carboxylic acid and primary amine, maleimide and thiol, hydrazide, an aldehyde, or a primary amine and/or aldehyde. As another example, the linker can bind to or comprise a reactive group, such as a thiol, an acrylate, an aldehyde, a hydrazide, or a tyramine.

In other embodiments, the linker can contain an amide, a thioether, a disulfide, an acetyl-hydrazone group, a polycyclic group, a click chemistry (CC) group (e.g., cycloadditions, for example, Huisgen catalytic cycloaddition; nucleophilic substitution chemistry, for example, ring opening of heterocyclic electrophiles; carbonyl chemistry of the "non-aldol" type, for example, formation of ureas, thioureas, and hydrazones; additions to carbon-carbon multiple bonds, for example, epoxidation and dihydroxylation); or a physical or chemical bond.

Binding Moiety

The synthetic dendritic cell can comprise a binding moiety. The binding moiety can be a moiety that can facilitate binding to a T cell activation agent, a linker, or a delivery agent, as described herein. The binding moiety can covalently or non-covalently bind to a T cell activation agent, a linker, or a delivery agent, as described herein. For example, the binding moiety can be a biotin binding protein conjugate, such as an avidin/biotin complex (e.g., avidin, streptavidin, neutravidin, or the like).

The binding moiety can be streptavidin (or avidin, neutravidin, or the like) that can non-covalently bind up to four biotin molecules. A linker (e.g., PEG) or a T cell activation agent (e.g., pMHC, anti-CD28, IL15/IL15Rα) can be biotinylated, thus attaching the streptavidin (SAv) to the linker. For example, the biotin moiety can be attached to the linker or T cell activation agent through enzymatic biotinylation, primary amine biotinylation, sulfhydryl biotinylation, carboxyl biotinylation, glycoprotein biotinylation, non-specific biotinylation, and the like. The linker can then attach to a substrate/delivery agent/matrix material (e.g., a hydrogel).

T Cell Activation Agent

A T cell activation agent can be one or more components that can, alone or in combination with other T cell activation agents, prime or activate T cells. For example, a synthetic DC can comprise one or more T cell activation agents. As another example, the T cell activation agents can be one or more components that allow the synthetic DC to mimic a DC response to activate T cells.

Dendritic cells are a key antigen-presenting cell type that activates T cells. Because DCs have a central role in controlling the immune response in cancer patients, properties of the synthetic DCs can mimic DCs. To prime T cells, DCs are known to deliver three signals which are thought to determine the fate of naive T cell differentiation (see e.g., FIG. 1A). As such, the synthetic DCs can comprise a T cell activation agent that can deliver these signals as well. Signal 1 is delivered through the TCR when it engages an appropriate peptide—MHC complex. Signal 1 alone is thought to promote naive T-cell inactivation by anergy, deletion or co-option into a regulatory cell fate, thereby leading to 'tolerance.' Signal 2 is referred to as to-stimulation' that, together with signal 1, induces 'immunity.' This is often measured as T-cell clonal expansion, differentiation into effector cells, and a long-term increase in precursor frequency ('memory'). Signal 2 is often equated with signaling through CD28 when it engages CD80 and/or CD86. However, CD80 and CD86 can also engage cytotoxic T-lymphocyte antigen 4 (CTLA4) and deliver tolerogenic signals to T cells. Thus, the actual 'signal 2,' which favors immunity, is likely to be a fine balance of positive and negative co-stimulatory signals emanating from many receptors. Tumor cells, or antigen presenting cells (APCs), present in the tumor, provide signal 1, and often a negative co-stimulation, resulting in T cell tolerance. Signal 3 refers to signals delivered from the APC to the T cell that determine its differentiation into an effector cell. IL-15 provided by a subset of skin DCs is critical for the differentiation of cytotoxic T lymphocytes (CTLs) and is therefore critical for the expansion of effector CD8$^+$ T cells. The relevance of these signals in inducing a robust CTL response against a subdominant T cell epitope is currently being explored.

As such, the T cell activation agent can (1) promote naive T-cell inactivation by anergy, deletion or co-option into a regulatory cell fate; (2) induce immunity; and or (3) induce differentiation of cytotoxic T lymphocytes (CTLs).

A T cell activation agent can comprise one or more agents that bind to T cell activation receptors or binding sites. For example, the T cell activation agent can comprise an agent that binds to CD28, IL15Rβ/IL2Rγ$_c$, or the T cell receptor (TCR). A T cell activation agent can comprise anti-CD28 (αCD28), IL-15/IL15Rα, IL-2, IL-7, IL-12, MHC, pMHC, CD70, CD40, or CDS. The T cell activation agent can comprise a cytokine or interleukin receptor.

As an example, T cell activation agent can comprise one or more compositions selected from the group consisting of a MHC or a non-classical MHC (e.g., CD1a, CD1c, CD1d), pMHC, a co-stimulatory factor, anti-CD28 (αCD28), CD70, CD40, CDS, CD80, CD86, or a cytokine and the corresponding cytokine receptor (e.g., Interleukin 15 (IL15)/IL-15Rα, IL-2, IL-7, IL-12).

In some embodiments, 'signal 1' (see above dendritic cell section) can be provided by MHC. For example, a T cell activation agent can be a multimeric (e.g., a pentamer) T cell activation agent. As another example, the T cell activation agent can be a MHC complex which can comprise MHC class I or MHC class II molecules. Furthermore, MHC class I components can correspond to the following human genes: HLA-A, HLA-B, HLA-C, and the like. Each gene is highly polymorphic; for example, there are over 2,000 known alleles of HLA-A, and within this subset there are over 400 known alleles of HLA-A2 (or HLA-A*02). For example, a common HLA class I allele is HLA-A201 (or HLA-A*0201), which is present in over 50% of Caucasians. Additional MHC haplotypes include but are not limited to A0101, A0301, A1101, A2402, A2601, B0702, B0801, B3701, B4001, B4402, C0501, or C0602. MHC class II can correspond to the following human genes, which are also highly polymorphic: HLA-DP, HLA-DM, HLA-DOA, HLA-DOB, HLA-DQ, HLA-DR, and the like. As another example, a T cell activation agent can be a non-classical MHC, such as CD1a, CD1c, or CD1d that present lipids and can be used to expand a patient's lipid-specific or antigen-specific cytotoxic T-lymphocytes (CTLs). The MHC or pMHC component used in the synthetic DC can correspond to the HLA alleles or haplotype present in the specific patient.

Furthermore, the MHC or pMHC component can be bound to peptides in order to elicit a response from antigen-specific T cells. A peptide can be any amino acid sequence varying from 8 to 30 amino acid residues long; MHC class I peptides are typically 8 to 10 residues long, while MHC class II can vary from 11 to 30 residues long. The peptides can have specific binding to various alleles of MHC class I or MHC class II. For example, the peptide can be high and low affinity melanocyte differentiation antigen MART-1 peptides (ELAGIGILTV (SEQ ID NO: 1) and AAGIGILTV (SEQ ID NO: 2), respectively). As another example, the high affinity HLA-A2-restricted influenza M1 peptide can be used. As another example, the peptide can be tumor-specific peptides selected from a patient's specific tumor cells. The peptides can also be in the form of multimers (e.g., tetramers).

In some embodiments, a T cell activation agent can be any agent that binds a T cell co-stimulatory receptor (e.g. CD28) to provide 'signal 2.' For example, the T cell activation agent can be CD80 (B7-1), CD86 (B7-1), B7-H2, or an anti-CD28 antibody. As another example, the agent can be any molecule that binds to another T cell co-stimulatory receptor (e.g. ICOS, CD27, and the like). For example, the T cell activation agent can be CD70, LIGHT, HVEM, CD40L, 4-1BBL, OX40L, TL1A, GITRL, CD30L, TIM4, SLAM, CD5, CD48, CD58, CD155, C112, and the like. Furthermore, the T cell activation agent can be an antibody against a T cell co-stimulatory receptor. These co-stimulatory molecules are well known in the art, as reviewed by Chen et al. Nat Rev Immunol. 2013 13(4): 227-242.

In some embodiments, a cytokine provides 'signal 3' for T cell activation. For example, a cytokine such as IL-15 can be introduced as a (IL15)/IL-15Rα complex. Additionally, IL-15 can be introduced as a soluble cytokine, or the newly developed IL-15 superagonist can be used (ALT-803; Altor Bioscience). Furthermore, additional cytokines produced by helper T cells (e.g., IL-2, IL-7) or other DC subsets (e.g., IL-12) can be used as they could be important for the proliferation and survival of the T cells; as such, these cytokines could also be conjugated to the PA surface or introduced in their soluble forms.

Auxiliary Components

The synthetic DCs and components thereof can include an auxiliary component. An auxiliary component can be a component that allows for a T cell activation agent to be multimeric. Other auxiliary components can be any biocompatible component such as a polymer or branched polymer such as a dendrimer. Another auxiliary component that can be included is a gelatin to encapsulate the T cells.

Formation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a proliferative disease (e.g., cancer), or chronic disease (e.g., chronic viral infections, HCV, HIV) in a subject in need administration of a therapeutically effective amount of synthetic DCs, so as to expand antigen-specific T cells.

A proliferative disease can include a pathology, tumor, or a cancer such as a prostate cancer; a breast cancer; a lung cancer; an esophageal cancer; a gynecologic cancer (e.g., ovarian, cervical, endometrial); an anal/rectal tumor; a sarcoma; a head or neck cancer; metastatic cancer; pancreatic cancer; skin cancer (e.g., basal cell, melanoma), colon cancer; leukemia; or lymphoma.

A chronic disease can be a chronic viral infection, HIV, or HPV.

Methods described herein are generally performed on a subject in need thereof. A subject in need of the therapeutic methods described herein can be a subject having, diagnosed with, suspected of having, or at risk for developing a proliferative disease. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of synthetic DCs is, for example, that amount that would cause the desired therapeutic effect in a subject while minimizing undesired side effects. In various embodiments, an effective amount of synthetic DCs described herein can substantially inhibit disease progression, slow the progress of disease, or limit the development of disease (e.g., disease caused by cancer or a chronic viral infection).

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of synthetic DCs can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit disease progression, slow the progress of disease, or limit the development of disease.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of synthetic DCs can occur as a single event or over a time course of treatment. For example, synthetic DCs can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a proliferative or chronic disease, disorder, or condition (e.g., cancer, chronic viral infection).

Synthetic DCs can be administered simultaneously or sequentially with another agent, such as an antibiotic, an anti-inflammatory, anti-viral, or another agent. For example, synthetic DCs can be administered simultaneously with another agent, such as an antibiotic, an anti-inflammatory, or anti-viral. Simultaneous administration can occur through administration of separate compositions, each containing one or more of synthetic DCs, an antibiotic, an anti-inflammatory, anti-viral, or another agent. Simultaneous administration can occur through administration of one composition containing two or more synthetic DCs, an antibiotic, an anti-inflammatory, or another agent. Synthetic DCs can be administered sequentially with an antibiotic, an anti-inflammatory, or another agent. For example, synthetic DCs can be administered before or after administration of an antibiotic, an anti-inflammatory, anti-viral, or another agent.

Administration

Agents and compositions described herein can be administered according to methods described herein in a variety of means known to the art.

The T cells (e.g., isolated T cells) can be administered to a subject after expanding them in vitro by the 2D synthetic DC.

As discussed above, administration can be intratumoral, implanted, parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), drug-releasing biomaterials, polymer matrices, gels, permeable membranes, osmotic systems, multilayer coatings, microparticles, implantable matrix devices, mini-osmotic pumps, implantable pumps, injectable gels, hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, or liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to delivery agents, linkers, binding moieties, or T cell activation agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Analysis of CTL Priming By LCs and Dermal DCs

The following example describes the priming of cytotoxic T lymphocytes (CTLs) by Langerhans cells (LCs) and dermal dendritic cells (DCs).

LCs Are Highly Efficient at Priming Tumor Specific CTLs

Figure 2:
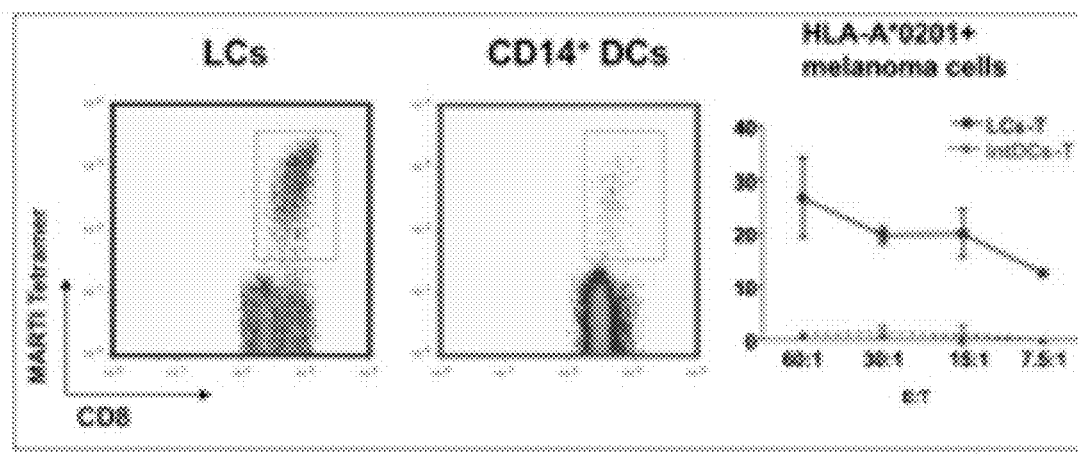
FIG. 2 is a series of flow plots and graphs showing that Langerhans cells (LCs) prime Mart1-specific CD8$^+$ T cells more efficiently than CD14$^+$ DCs, as measured by the percentage of tetramer-binding cells (left). CD8$^+$ T cells primed by LCs, but not CD14$^+$ DCs, are able to kill melanoma cells (right) (Klechevsky et al Immunity 2008).

Studying the biology of skin DC subset is important to work toward the goal of designing novel vaccines and immunotherapies for viral infections or cancer. The healthy human skin contains multiple DC populations. Langerhans cells (LCs) are the major DC in the epidermis and DCs in the dermis and are identified based on the expression of CD1a and CD14. Co-cultures of antigen loaded LCs with naïve $CD8^+$ T cells showed that LCs were very efficient at priming and cross-priming naïve $CD8^+$ T cells compared to the dermal $CD14^+$ DCs (see e.g., FIG. 2). The T cells primed by LCs had a high avidity TCR and were able to efficiently kill cancer cell lines (see e.g., FIG. 2). Comparative genomic analysis of the mouse DC subsets has revealed that human LCs share functional genes related to class I antigen presentation with the mouse $CD8a^+/CD103^+$ DCs, a subset of DCs that was shown to be critical for CD8+ T cell expansion and tumor therapy in clinical models.

Figure 3:
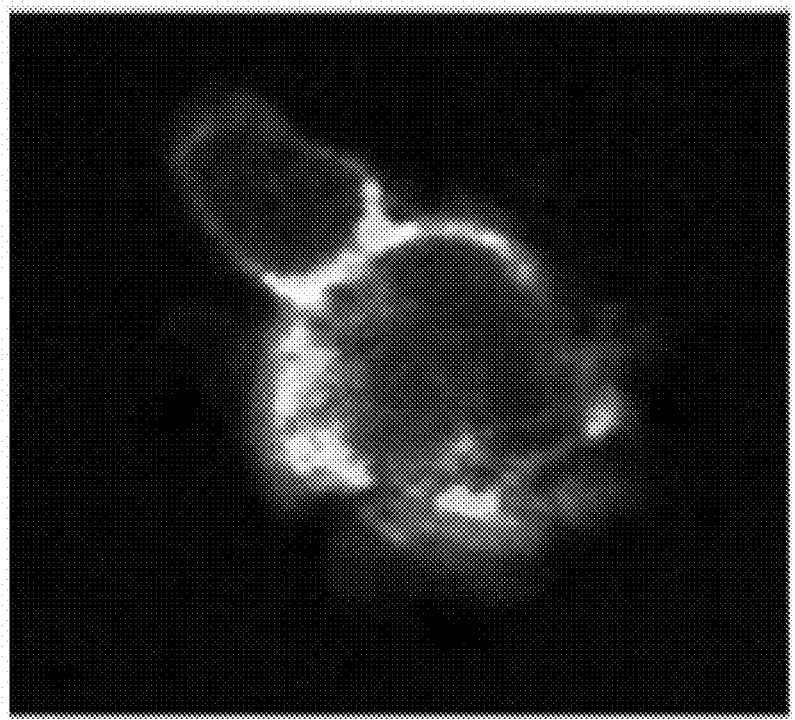
FIG. 3 is a fluorescence micrograph showing that IL-15 is localized at the immunological synapse between LCs and naïve CD8$^+$ T cells (Banchereau et al Blood 2012).

Balance Between Positive and Negative Co-stimulatory Molecules and Cytokines Controls CTL Priming The ability of LCs to prime effector responses is a critical step in the initiation of an autoimmune disease, but also a desirable vaccine response. It is imperative to discover features of LCs that allow them to prime effector responses. The set of cytokines produced by this DC subset might account for their unique function. Thus, cytokine expression patterns were analyzed from LCs and dermal $CD14^+$ DCs, which were sorted from the epidermis or dermis by microarray. It was shown that IL-15 is produced by LCs, it localized at the immunological synapse with naïve $CD8^+$ T cells (see e.g., FIG. 3), and blocking IL-15 inhibited CTL priming. Therefore, IL-15 is included as a third signal for CTL priming. Human dermal $CD14^+$ DCs also produce IL-10, which promotes $CD4^+$ Treg development. The secretion of IL-10 and TGF-β impairs the ability of dermal DCs to prime CTLs. In addition, the unique expression of the immunoglobulin-like transcript (ILT) receptors, ILT2 and ILT4, on dermal $CD14^+$ DCs attenuates cellular immune responses. Therefore, these examples can use approved drugs (or agents) to neutralize negative co-stimulatory regulator on T cells such as CTLA-4, PDL-1, PD-1, IL13R, or IL4R which can engage negative co-stimulatory molecules on the tumor.

Example 2: Development of Mechanically Optimized Synthetic DCs Providing Three Signals For Efficient T Cell Expansion The current methods for expanding T cells rely on a non-specific activation of patient T cells, including the regulatory T cells. There is a clear need for a controlled and robust expansion of tumor specific T cells, which are often against suboptimal epitopes and are masked by an immunosuppressive microenvironment. It has been demonstrated that some DC subsets are particularly adept for activating antigen-specific T cell responses. Because using an individual patient's DCs for T cell expansion would be an extremely costly and time-consuming proposition, a synthetic DC (comprising these same features) is a more economical and modular alternative for tailoring T cell expansion that is unique to the patient. Thus, a new method to target specific T cells in precise ways is being developed, which will allow fine-tuning of desired immune responses, improve the efficacy of existing adaptive cell therapy, and reduce toxicity and side effects.

Human $CD4^+$ and $CD8^+$ T cells can sense the stiffness of their adherent substrate and exhibit significantly higher proliferation on softer matrices. In addition, incorporating a linker between the hydrogel polymeric molecules and the T-cell activating molecules can enhance flexibility of the tethered molecules and facilitate their clustering. Finally, use of a multimeric pMHC complex enhances the binding avidity and further promotes TCR clustering. Integrating soft matrices, $PEG_4$ linker, and multimeric pMHC maximizes the expansion of subdominant epitope-specific T cells through enhanced engagement with co-stimulation molecules and TCR clustering.

Experiments are carried out using cells from, for example, HLA-A201+ individuals, a common HLA class I allele, which is present in about 50% of Caucasians. The selection of HLA-A201+ patients permits the use of many of the tools validated by previous studies. Thus, this synthetic DC model consists of presenting HLA-A2/peptide complexes on soft hydrogels of tunable stiffness for expanding specific CD8+ T cells. In addition to pMHC, the role of additional co-stimulation signals αCD28 and IL15/1L-15Rα in expanding specific T cells is being evaluated. Checkpoint blockade inhibitors against anti-CTLA-4 or PD-1 are also introduced to evaluate their role in neutralizing the existing regulatory T cells in the blood.

Peptide-MHC Complexes

Peptide-MHC-fusion molecules were shown to induce T cell activation in vitro, monitored by the peptide-specific release of IFNγ from these T cell clones/lines, as well as to mobilize CTL to tumors or to the site of viral infected cells in vivo. Here commercially available biotin-labeled HLA-A2 pentamers are used (Proimmune). The biotin allows for the mobilization of the pentamer to the surface of the matrix, and the multiple pMHC arms allows for increased TCR binding avidity and clustering.

Functionalized Alginate-gelatin Hydrogel-based Synthetic DCs of Tunable Stiffness Oxidized alginate-gelatin covalently cross-linked (ADA-GEL) hydrogels of varying ADA to GEL ratios can be fabricated. Here, gel stiffness can be varied between 1-30 kPa by choosing various ratios of ADA and GEL and by varying concentration of calcium in ionic gelation solution (calcium chloride). Streptavidin (SAv) is conjugated to the ADA using a bi-functional hydrophilic polyethylene glycol (PEG)-based linker, biotin-$PEG_4$-hydrazide (ThermoFisher). Biotin of the linker binds to the SAv molecules. Hydrazide compound, at the other end of the linker, contains a primary amine group that can bind to the free aldehyde group of the ADA compound through Schiff base formation. GEL solution is added to the SAv-conjugated ADA solution and films are prepared by casting the resultant mixer into a Petri dish and subsequently crosslinking with calcium chloride solution. Final stiffness of the ADA-GEL hydrogels is measured using Atomic Force Microscopy (AFM). To incorporate the four signals required for T cell activation, a mixture of pMHC, anti-CD28 (αCD28), and Interleukin 15 (IL15)/IL-15Rα complex is conjugated onto the streptavidin-laden ADA-GEL surface. Conjugation of SAv to the hydrogel matrix is verified through visualization using a fluorochrome-labeled SAv (Cy3 Streptavidin, Vector Labs).

Assessment of T Cell Activation Due to Different Signals

The different signals provided by the synthetic DCs are compared for their ability to activate CTL responses. To assess primary and memory antigen specific CD8+ T cell responses, a tumor and a viral antigen is used as a model. High and low affinity melanocyte differentiation antigen MART-1 peptides (ELAGIGILTV (SEQ ID NO: 1) and AAGIGILTV (SEQ ID NO: 2), respectively) are used to assess primary responses, and influenza M1 peptide is used to measure secondary responses. Naïve T cells, that are sorted based on their CCR7 and CD45RA expression, are cultured for 3-10 days on synthetic DC substrates. The phenotype of the proliferating T cells is analyzed at various time points. HLA-A201 based tetramers are useful to measure the frequency of a specific CD8+ T cell in cultured T cell lines. The proliferation of CD8+ T cells is assessed by the numbers of tetramer positive cells. The high affinity HLA-A2-restricted influenza peptide is used as a control. The expansion of the influenza specific memory CD8+ T cells, which are present in high frequency in the blood of healthy individuals serves as a positive control. De-identified healthy T cells are obtained from the Mississippi Valley regional blood center (MVRBC). T cells are obtained from both sexes to prevent bias.

CTL Characterization

At various time points, the quality of the expanded CTLs is assessed based on intracytoplasmic expression of cytotoxic/cytostatic effector molecules such as granzyme A, B, perforin and granulysin by flow cytometry, and polyfunctionality is assessed by the expression of TNF-α, IL-2 and IFN-γ or by the presence of these cytokines in the culture supernatant using Luminex. Bcl-2 expression predicts cell survival. For a killing assay, an HLA-A201+ cell line is used that is loaded or not with the relevant peptide, or HLA-A201+ melanoma cell lines expressing the endogenous MART-1 as targets can also be used in a standard $Cr^{51}$-release assay. T cells are incubated with a target cell line at various ratios and are evaluated for the conditions that induce T cells with a high killing capacity at a high T cell to target ratio. Moreover, CD107a-mobilization to the surface is assessed by flow cytometry in response to target cells to assess their effector capacity.

Data Interpretation

Because a subset of CD8+ T cells, which are specific for the low affinity peptide and possess effector function, are primed by our synthetic DCs, we consider this to be strong evidence in support of this design. The presence of checkpoint blockade can increase the frequency of the effector, polyfunctional (IFN-γ/TNF-α/IL-2), long-lived (Bcl-2) T cell responses. This example also helps establish signals required to achieve an optimal T cell expansion of subdominant epitopes. These measurements across varying PA stiffness indicate optimal material properties for fabricating synthetic DCs to various MHC specificities.

Additional Approaches and Applications

Figure 4:
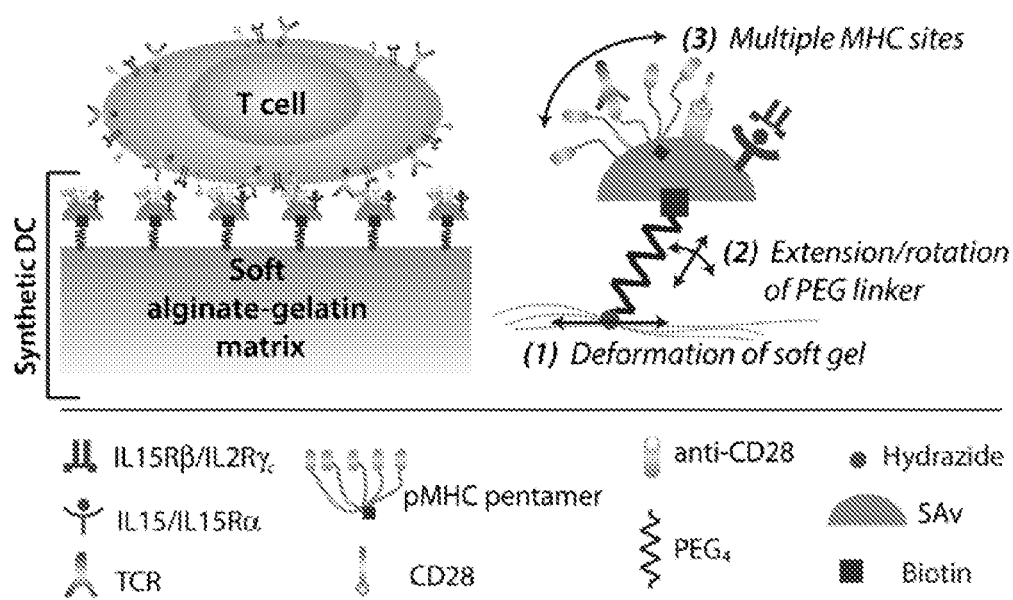
FIG. 4 is a schematic describing enhanced engagement of effector molecules and TCR clustering by combining three factors: (1) displacement through deformation of a soft gel, (2) extended reach through a PEG linker, and (3) multiple sites provided by the pMHC pentamer.

Even with the three factors used in combination to enhance TCR clustering (see e.g., FIG. 4), this system does not exactly mimic the fluidity available on DC membranes. However, this is a necessary compromise for capturing DC-like properties onto a substrate. At the very least, this proposed system could be more effective than any other existing platforms for T cell activation through interaction with DC-mimicking environments.

In the current embodiment, IL-15/IL15R is conjugated to the PA surface. Alternatively, IL-15 can be introduced as a soluble cytokine or the newly developed IL-15 superagonist can be used (ALT-803; Altor Bioscience). Additional cytokines produced by helper T cells (IL-2, IL-7) or other DC subsets (such as IL-12) could be important for the proliferation and survival of the T cells; as such, these cytokines could also be conjugated to the PA surface or introduced in their soluble forms.

The checkpoint blockade could impact the quantity of the T cell response, and it could also affect the quality of the induced $CD8^+$ T cells. In the presence of anti-CTLA-4 or PD-1, the effector T cells should be selectively expanded rather than regulatory T cells.

The current embodiment focuses on HLA-A201$^+$ cells. Additional studies can be conducted with other MHC haplotypes. Additional haplotypes include, but are not limited to the following recombinant MHCs: A0101, A0301, A1101, A2402, A2601, B0702, B0801, B3701, B4001, B4402, C0501, or C0602 (Rodenko et al. (2006) Nat Protoc 1(3): 1120-1132). Non classical MHC molecules including CD1a, CD1c, CD1d can also be used. A variety of tumor-specific peptides can also be used. These studies can help confirm that this customizable synthetic DC platform could be individualized to patients across different haplotypes.

Example 3: Fabrication of the Stiffness-Optimized Micro-DCs for T Cell Growth in the Form of 3D Microcapsules Adoptive T cell therapy requires 3D micro-carriers for expanding and delivering tumor-reactive T cells next to the tumor site. Moreover, this transportable form of T cells in micro-capsules/beads can also be used as a vaccine for expanding tumor specific T cells in the patient. The naturally-derived hydrogels are found to be appropriate for cell encapsulation due to their excellent biocompatibility, biodegradability, and very low cytotoxicity. Among the naturally-derived hydrogel-forming materials, alginate is extensively used in cell encapsulation because of its rapid ionic gelation with divalent cations. The limitations of alginate due to poor cell adhesion and slow and uncontrolled degradation have been successfully overcome by incorporation of gelatin into the chemically modified alginate. This example shows the encapsulation of T-cells within alginate-based hollow-core microcapsules. The alginate-gelatin composition used corresponds to the matrix stiffness optimized in Example 2. This approach is different from existing ones due to several reasons, including IL-15/IL-15R bound to the surface, a checkpoint blockade during the priming, and the three integrated factors (see e.g., FIG. 4) for TCR clustering.

Cell Encapsulation Within Hollow-core Microcapsules

Going from stock T cells to the expanded population of activated T cells within a hollow-core microcapsules platform is executed in these sub-steps:

Step 1: Stock T Cells in Gelatin Microspheres

A 5% (w/v) gelatin solution is prepared in calcium-free Krebs Ringer Hepes buffer solution (CF-KRH, pH 7.4) at 37° C. and sterilized by filtration through a 0.22 μm filter. T cells are dispersed into the gelatin solution at a density of $1 \times 10^7$ cells/mL. T cells-encapsulated gelatin microspheres are generated with a co-axial droplet generator (see e.g., FIG. 5A). Through the generator, gelatin solution dispersed with cells is extruded from a 27-gauge needle into a co-flowing immiscible stream of lecithin containing liquid paraffin at 37° C. The size of the gelatin microsphere can be tuned by changing the flow rates and needle size. Cell-embedded gelatin microspheres are thermally gelled in an ice bath for 10 min. Paraffin is removed by washing the microspheres with cold CF-KRH (4° C.).

Step 2: Encapsulation of Microspheres Within ADA

These gelatin microspheres are enclosed by pMHC-αCD28-IL15/IL15Rα-SAv-conjugated ADA microcapsules, which are prepared using an electrostatic droplet generator. Note that the conjugation of pMHC-αCD28-IL15/IL15Rα molecules with ADA, through SAv, activates T cells (see e.g., Example 2). The T cell-containing gelatin microspheres are dispersed into pMHC-αCD28-IL15/IL15Rα-Sav-conjugated 5% ADA solution and the mixture is transferred into an extrusion cartridge equipped with a 26-gauge needle, which is connected to the high voltage DC generator. A gelation bath containing calcium chloride ($CaCl_2$) of varying concentrations is placed underneath the extrusion cartridge. The gelation bath is connected to the other end of the high voltage generator. The T cell-containing gelatin microspheres are embedded within the aforementioned ADA matrix by extruding the solution and dropping into the gelation bath under an applied voltage. These microcapsules are kept in the $CaCl_2$ solution for 10 minutes to allow complete ionic gelation. To remove the residual calcium chloride solution from the surface of the microcapsules, the fabricated microcapsules are sieved using a cell strainer and washed three times with serum-free cell culture medium.

Step 3: Liquification of Gelatin to Enable T Cell Interaction with ADA Matrix

Activation of T cells requires a direct contact with the pMHC-αCD28-IL15/IL15Rαcomplex conjugated to the surrounding ADA matrix. To enable this interaction, the inner core gelatin gel is liquefied at 37° C. as shown in FIG. 5B. Note that the use of oxidized alginate (ADA), which has lower molar mass with oxidized G units of polysaccharide chain. It has been already shown that the ADA-GEL hydrogel possesses high porous structure, which should allow efficient diffusion of gelatin, especially because gelatin possesses a low molar mass with shorter molecular chains when it is in liquid state. Thus, the liquefied gelatin diffuses into the ADA polymer networks, reacts with the ADA, and thus the covalently cross-linked ADA-GEL hydrogel is formed. The porosity of the gel can be increased by changing the oxidation of ADA.

Step 4: Expansion and Extraction of T Cells

The embedded cells proliferate within the microcapsules over time during incubation in an appropriate culture medium. Simultaneously the T-cells are activated by the three signals—pMHC, biotinylated antibodies (αCD28), and IL15/IL-15Rα—tethered through SAv, as schematically shown in FIG. 5B. After 5-8 days of incubation, the embedded T-cells are retrieved by dissolving the hydrogel using either a calcium chelator (e.g. sodium citrate) or alginate lyase.

In-vivo Validation of Activated T Cells in Micro-capsules

The expanded T cells are validated through methods described in Example 2. The capacity of MART-1-specific CD8 T cells induced by micro-DCs to reject melanoma tumor in vivo is analyzed by injecting NSG (NOD-scid IL2Rγ$^{null}$ Jackson stock 005557) mice intraepidermally with an HLA-A2+ melanoma cell line that expresses the MART-1 protein (Mel526). The panel of melanoma cell lines also includes MART-1− and HLA-A2− lines that can be used as controls. Tumor size is monitored every 2-3 days following inoculation. Tumor volume (ellipsoid) is calculated as follows: short diameter×long diameter/2. When the tumor has reached a detectable size, $10^6$ of the expanded T cells are adoptively transferred with or without checkpoint blockade inhibitors anti-CTLA-4 and/or anti-PD-1. Tumor size is monitored every 2-3 days for 30 days following adoptive cell transfer. In addition to tumor growth, specific CD8+ T cells in the tumor are characterized by intracellular staining for IFN-γ, TNF-α, IL-2, granzymes and perforin after MART-1 re-stimulation. CD8+ T cells infiltrating the tumor are also evaluated for further proliferation and upregulation of activation (CD24, ICOS, 41BB), or inhibitory exhaustion markers (PD-1, Lag-3, Tim3, TIGIT).

Data Interpretation

Two key parameters are used to assess the success of these studies. Since structural integrity of T cell-embedded microcapsules remains stable over the culture period, these capsules could be regarded stable enough to serve as implants near the tumor site. Thus, these T cell-embedded micro-DCs can aid targeted and efficient therapy, requiring lower number of T cells for similar results. Second, as the T cell expansion rate remains comparable to that measured in Example 2, the benefit of the transportability of 3D beads does not significantly sacrifice the expansion efficiency of 2D surfaces. The MART-1-specific T cells could eliminate the established tumor and display high amounts of effector molecules with low inhibitory surface receptors. The presence of checkpoint blockade mAb can prevent T cell exhaustion within the tumor microenvironment and can increase local T cell proliferation. Subsequent work focuses on establishing the expansion of these encapsulated tumor-specific T cells in vivo.

Additional Approaches and Applications

Here, the gel stiffness is tuned through the calcium concentration of the hardening solution and the ratio of ADA and GEL. Alternatively the stiffness of the ADA-GEL hydrogel can also be varied by tuning the degree of oxidation of ADA. Higher oxidization of ADA leads to fewer G units since the oxidation happens preferentially in the G unit of polysaccharide chain. This can hamper ionic gelation by calcium chloride and that can eventually reduce stiffness. Since these studies focus on human T cells, this system can be transferred to a humanized mouse model exhibiting an intact human immune system, using the CRISPR/Cas9-based genome editing technology to facilitate the reconstitution of the entire human myeloid compartment, which is unique to skin. This model can be used to assess the role of these mechanically-optimized DCs in initiating the expansion of antigen-specific T cell responses in vivo and to investigate how they interact with and kill a syngeneic tumor. Moreover, this model can assess whether the 3D-DC micro-capsules can help establish broader T cell responses against subdominant tumor epitopes with or without checkpoint blockade therapy. These studies establish a proof of principal for using mechanically optimized DCs to expand naïve T cell epitopes. These mechanically optimized DCs could also be used for expanding individualized suboptimal patient unique/mutated cancer epitopes, which can be predicted by sequencing the patient tumor. These studies can be performed with cancer (e.g., melanoma) patients' blood and tumors that are engrafted in a humanized mouse model. In sum, these studies represent an important step forward in harnessing this inventive immunoengineering approach for devising new immunotherapy strategies for cancer patients.

Figure 6:
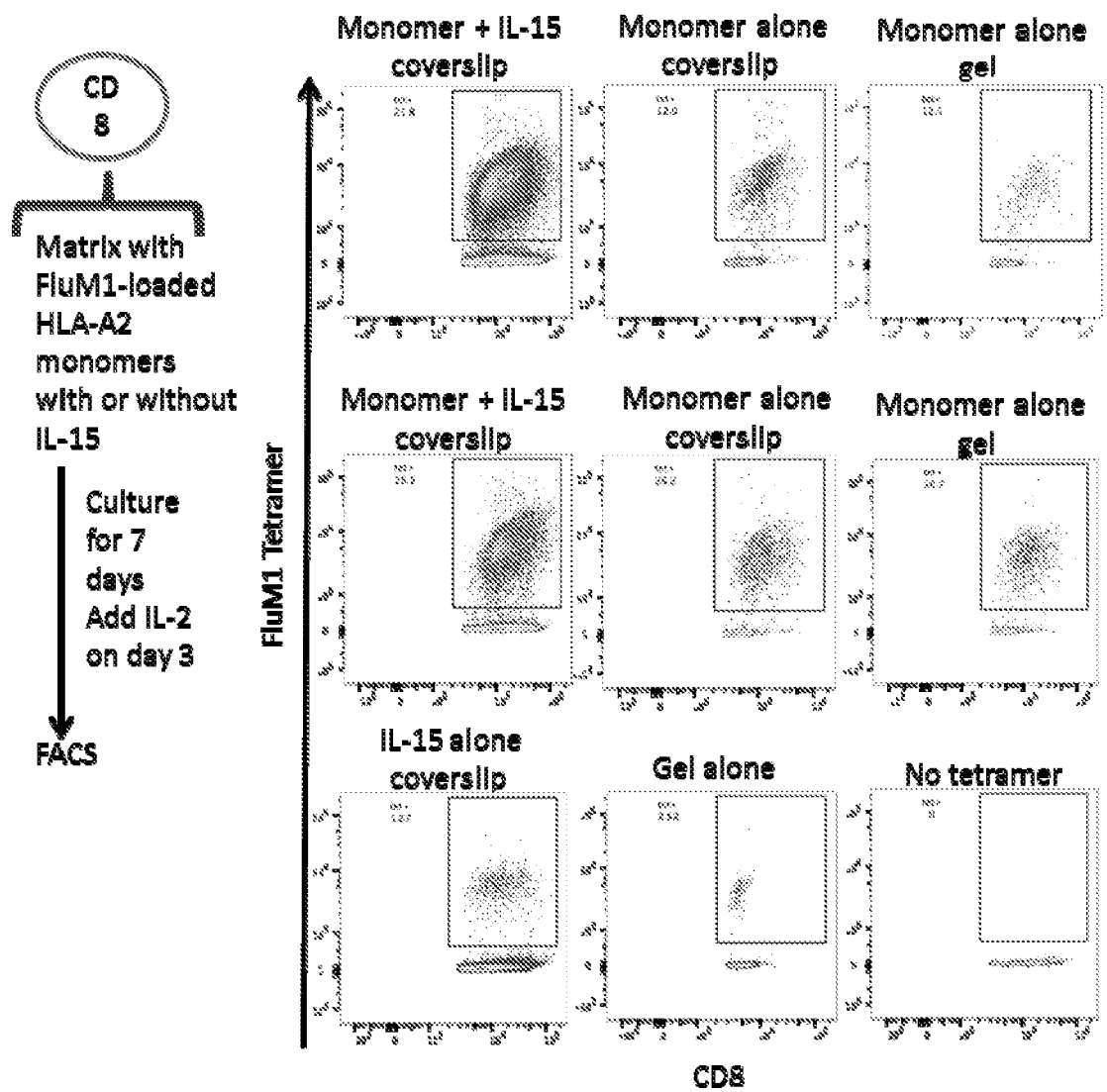
FIG. 6 is a series of images showing plots of the percentages of FluM1-specific CD8+ T cells that were expanded on the different matrix forms.

Example 4: FluM1-Loaded HLA-A2 Monomers With or Without IL-15 in Soft or Stiff Matrices Purified CD8+ cells from an HLA-A2+ donor were cultured on stiff or soft matrix (in gel or on cover slips) for 7 days. FluM1-loaded HLA-A*02:01 biotinylated monomers and IL-15 were added where indicated. On day 3, IL-2 was added to all wells. On day 7, flow cytometry analysis was performed to evaluate the number of Flu-specific CD8+ T cells by incubating the expanded cells with HLA-A2/FluM1 tetramer CD3, CD4, CD8, CDS, and CD25. Purified CD8+ cells from an HLA-A2+ donor were cultured on stiff or soft matrix (in gel or on cover slips) for 7 days. FluM1-loaded HLA-A*02:01 biotinylated monomers and IL-15 were added where indicated. On day 3, IL-2 was added to all wells. On day 7, flow cytometry analysis was performed to evaluate the number of Flu-specific CD8+ T cells by incubating the expanded cells with HLA-A2/FluM1 tetramer CD3, CD4, CD8, CD5, and CD25. Plots show the percentages of FluM1-specific CD8+ T cells that were expanded on the different matrix forms (see e.g., FIG. 6).

Figure 7:
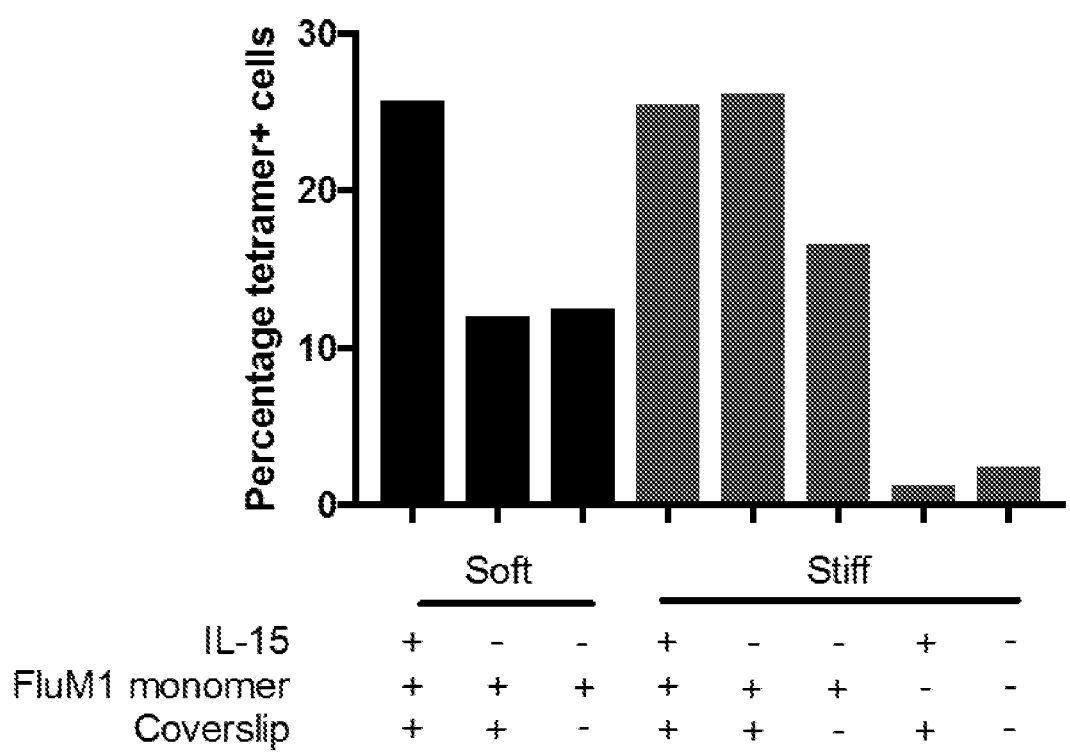
FIG. 7 is a bar graph showing the percentage of CD3+ CD8+ cells which are FluM1 tetramer+ and which grew on coverslips or on matrix gels (cover slips-).
Figure 8:
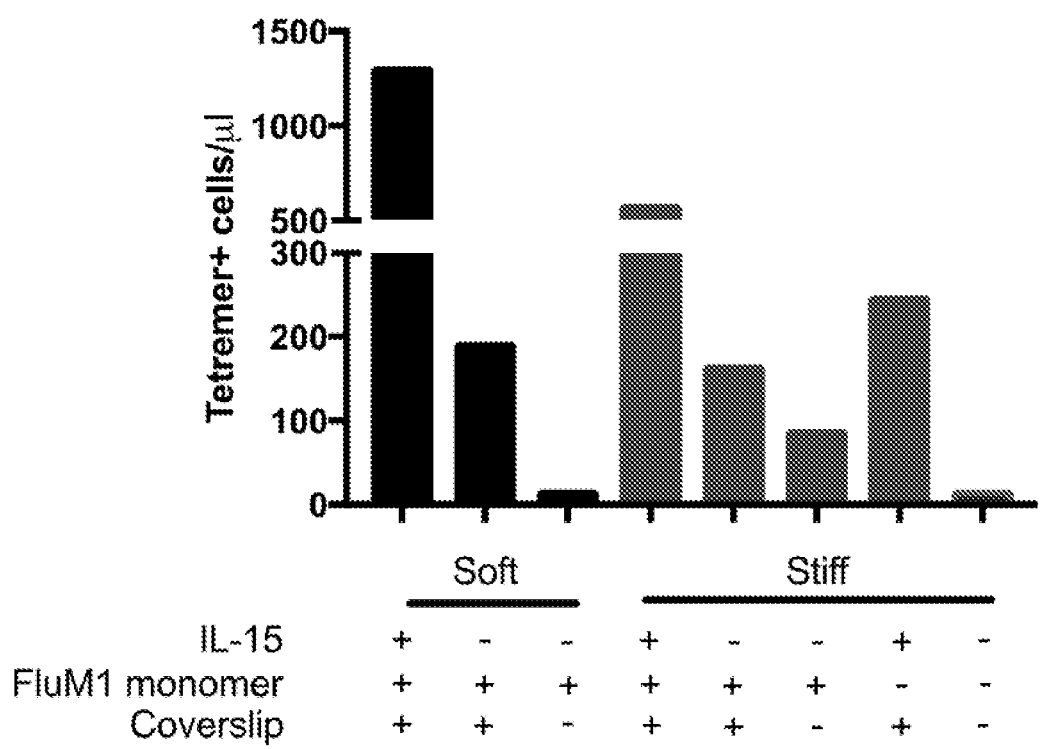
FIG. 8 is a bar graph shows the absolute number of T cells/μl in the distinct cultures.

The graph in FIG. 7 shows the percentage of CD3+ CD8+ cells which are FluM1 tetramer+ and which grew on coverslips or on matrix gels (cover slips-). In the absence of HLA-A*02:01 monomers, there is little to no expansion of FluM1-reactive CD8+. There is noticeable increases in FluM1-tetramer+CD8+cells when the monomer is added. IL-15 promotes the expansion of CD8+ FluM1-reactive T cells compared to wells without IL-15. There is a difference in the expansion of the cells based on the stiffness of the matrix.

The graph in FIG. 7 shows the absolute number of T cells/μl in the distinct cultures. The presence of HLA HLA-A*02:01 expanded CD8+ FluM1+ cells to a greater extent than wells without HLA-A*02:01. IL-15 promotes the expansion of CD8+ FluM1-tetramer+. This is more obvious than in the percentage graph. There is a difference in the expansion of the cells based on the stiffness of the matrix.

Figure 9:
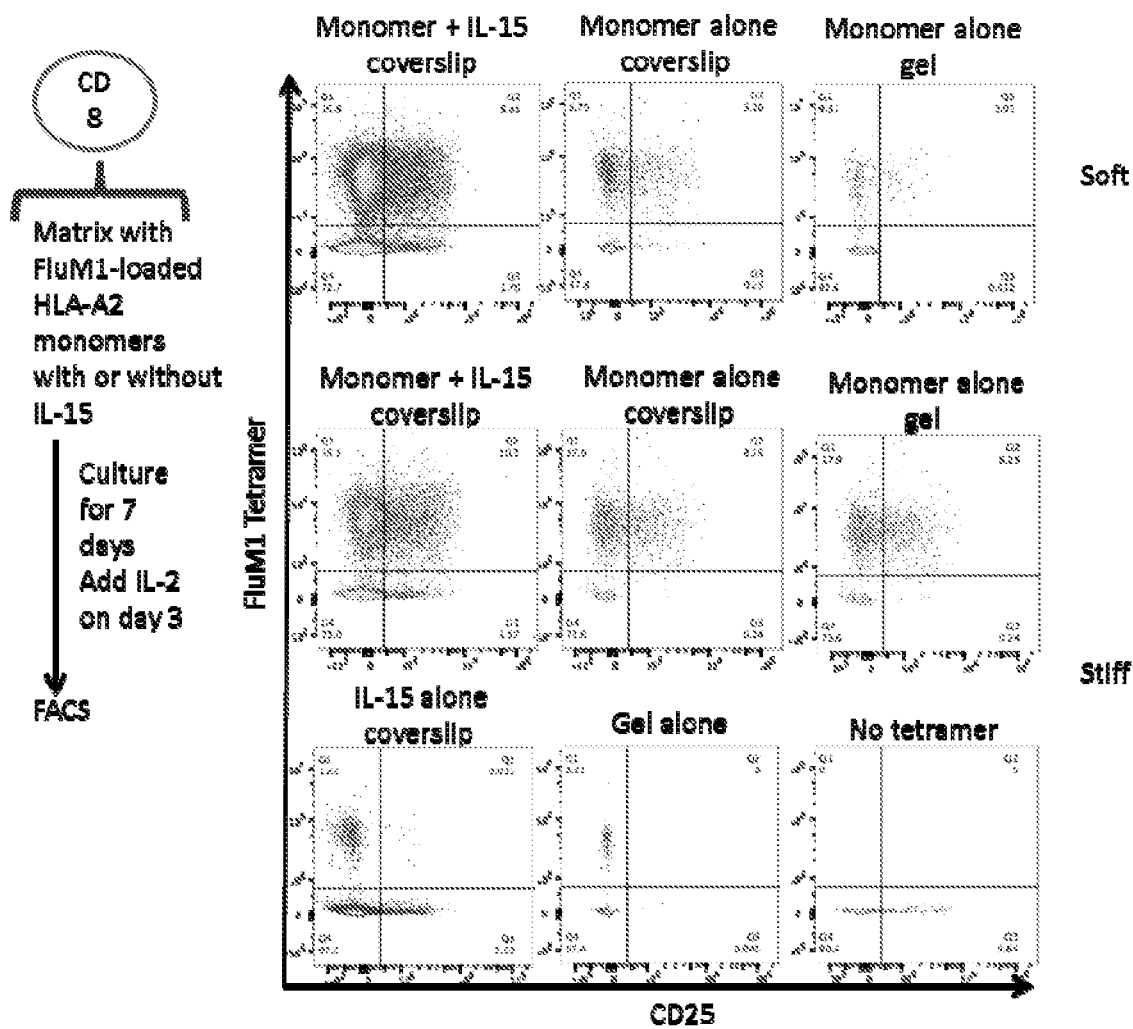
FIG. 9 is a series of images showing plots of the expression of CD25 on FluM1-specific CD8+ T cells that were expanded on the different matrix forms.

Purified CD8+ cells from an HLA-A2+ donor were cultured on stiff or soft matrix (in gel or on cover slips) for 7 days. FluM1-loaded HLA-A*02:01 biotinylated monomers and IL-15 were added where indicated. On day 3, IL-2 was added to all wells. On day 7, flow cytometry analysis was performed to evaluate the number of Flu-specific CD8+ T cells by incubating the expanded cells with HLA-A2/FluM1 tetramer CD3, CD4, CD8, CD5 and CD25. Plots (see e.g., FIG. 9) show the expression of CD25 on FluM1-specific CD8+ T cells that were expanded on the different matrix forms.

The graph (see e.g., FIG. 10) show the percentage of the Tetramer+ cells which are CD25+. IL-15 increased the percentage of tetramer+ CD25+ cells. The different matrix influenced the number of tetramer+ CD25+ cells.

Figure 11:
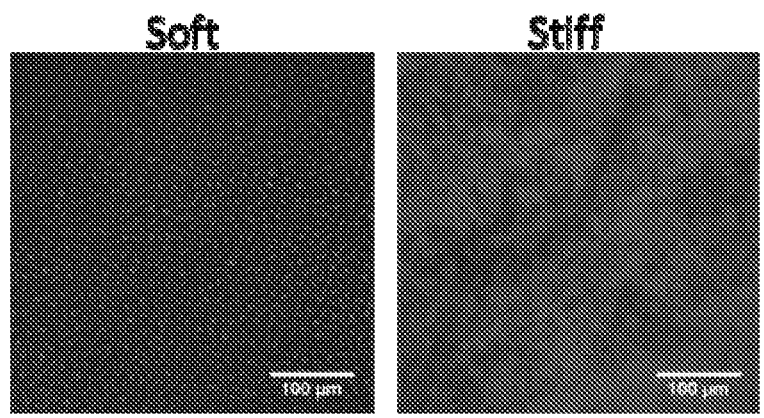
FIG. 11 is a series of confocal microscopy images of APC-conjugated streptavidin in oxidized alginate-gelatin covalently crosslinked (ADA-GEL) hydrogels.

Confocal microscopy images of APC-conjugated Streptavidin in Oxidized alginate-gelatin covalently crosslinked (ADA-GEL) hydrogels are shown in FIG. 11. APC-conjugated SAv appeared in red. Young's moduli of soft and stiff hydrogels with varying oxidized alginate and gelatin ratio, are 1 kPa and 10 kPa, respectively. APC-conjugated SAv was conjugated to the ADA using a bi-functional hydrophilic polyethylene glycol (PEG)-based linker, biotin-PEG4-hydrazide. Gelatin solution was added to the SAv-conjugated ADA solution that resulted covalent crosslinking between aldehydes of oxidized alginate and primary amines of gelatin. Further ionic crosslinking of the gel was performed using calcium chloride.

What is claimed is:

1. A synthetic dendritic cell (synthetic DC) comprising:
   a delivery agent, wherein the delivery agent is a hydrogel substrate comprising an oxidized alginate-gelatin covalently cross-linked (ADA-GEL) hydrogel;
   a linker;
   a binding moiety; and
   at least one T cell activation agent;
   wherein the linker is coupled to the delivery agent, the binding moiety is coupled to the linker, and the T cell activation agent is coupled to the binding moiety; and
   wherein the synthetic DC is capable of initiating activation and expansion of T cells.

2. The synthetic DC of claim 1,
   wherein the delivery agent has a stiffness between about 1 kPa and about 30 kPa.

3. The synthetic DC of claim 1,
   wherein the linker comprises a bi-functional hydrophilic polyethylene glycol (PEG)-based linker; and
   wherein the linker provides a flexible, extended reach to provide improved access to a T cell.

4. The synthetic DC of claim 1, wherein the binding moiety comprises avidin, streptavidin, or neutravidin.

5. The synthetic DC of claim 1, wherein the T cell activation agent comprises
   one or more compositions selected from the group consisting of a MHC, a non-classical MHC, CD1a, CD1c, CD1d, pMHC, anti-CD28 (αCD28), CD70, CD40, CD5, CD80, CD86, and a cytokine and corresponding cytokine receptor selected from Interleukin 15 (IL15)/IL-15Rα, IL-2, IL-7, IL-12, or 4-1BBL; and OX40L.

6. The synthetic DC of claim 1, wherein the T cell activation agent comprises one or more compositions selected from the group consisting of MHC, pMHC, anti-CD28 (αCD28), Interleukin 15 (IL15)/IL-15Rα, IL-2, IL-7, IL-12, CD1a, CD1c, CD1d, CD70, CD40, CD5, CD80, or CD86; and wherein the T cell activation agent is conjugated to a peptide or peptide tetramer, or wherein the T cell activation agent is multimeric.

7. The synthetic DC of claim 1, comprising one or more agents capable of neutralizing negative co-stimulatory regulators on T cells selected from the group consisting of anti-CTLA-4, anti-PDL-1, anti-PD-1, anti-IL13R, or anti-IL4R.

8. The synthetic DC of claim 1, in fluid contact with T cells provided by a subject in need of a therapeutic treatment.

9. The synthetic DC of claim 8, wherein the synthetic DCs enable a high-throughput production of subject-specific T cells.

10. A method of generating a synthetic dendritic cell (DC) comprising:
    (i) providing a hydrogel delivery agent comprising an oxidized alginate-gelatin covalently cross-linked (ADA-GEL) hydrogel;
    (ii) providing a linker;
    (iii) providing a binding moiety;
    (iv) providing one or more T cell activation agents;
    (v) coupling the linker to the hydrogel delivery agent;
    (vi) coupling the linker to the binding moiety; and
    (vii) coupling the binding moiety to the one or more T cell activation agents.

11. A method of activating T cells comprising:
    (i) providing a synthetic DC according to claim 1; and
    (ii) providing a T cell in fluid contact with the synthetic DC.

12. A method for expanding T cells against individualized tumor-specific mutational antigens or shared antigen comprising:
(i) providing T cells, optionally from a tumor biopsy or blood;
(ii) providing a synthetic DC of claim 1;
(iii) activating the T cells comprising contacting the T cell and the synthetic DC;
(iv) incubating the T cells and the synthetic DC for a period of time sufficient to induce T cell activation; and
(v) administering the activated T cells to a subject.

13. A method of treating cancer or chronic disease in a subject in need thereof comprising:
(i) providing T cells, optionally from a tumor biopsy or blood;
(ii) providing a synthetic DC of claim 1;
(iii) activating the T cells comprising contacting the T cell and the synthetic DC;
(iv) incubating the T cells and the synthetic DCs for a period of time sufficient to induce T cell activation; and
(ii) administering the activated T cells to the subject.

* * * * *